(12) United States Patent
Abolfathi

(10) Patent No.: US 9,185,485 B2
(45) Date of Patent: *Nov. 10, 2015

(54) METHODS AND APPARATUS FOR PROCESSING AUDIO SIGNALS

(75) Inventor: Amir A. Abolfathi, Woodside, CA (US)

(73) Assignee: Sonitus Medical, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/526,923

(22) Filed: Jun. 19, 2012

(65) Prior Publication Data

US 2012/0321113 A1    Dec. 20, 2012

Related U.S. Application Data

(63) Continuation of application No. 12/862,933, filed on Aug. 25, 2010, now Pat. No. 8,233,654, which is a continuation of application No. 11/672,271, filed on Feb. 7, 2007, now Pat. No. 7,801,319.

(60) Provisional application No. 60/809,244, filed on May 30, 2006, provisional application No. 60/820,223, filed on Jul. 24, 2006.

(51) Int. Cl.
*H04R 1/08* (2006.01)
*H04R 25/00* (2006.01)
(Continued)

(52) U.S. Cl.
CPC .. *H04R 1/46* (2013.01); *A61C 5/00* (2013.01); *A61C 8/0098* (2013.01); *H04R 3/04* (2013.01);
(Continued)

(58) Field of Classification Search
CPC .......................................................... H04R 1/08
USPC ................................................. 381/326, 380
See application file for complete search history.

(56) References Cited

U.S. PATENT DOCUMENTS 2,045,404 A    6/1936 Nicholides
2,161,169 A    6/1939 Jefferis
(Continued)

FOREIGN PATENT DOCUMENTS

EP    0715838 A2    6/1996
EP    0824889 A1    2/1998
(Continued)

OTHER PUBLICATIONS

"Special Forces Smart Noise Cancellation Ear Buds with Built-In GPS," http://www.gizmag.com/special-forces-smart-noise-cancellation-ear-buds-with-built-in-gps/9428/, 2 pages, 2008.
Altmann, et al. Foresighting the new technology waves—Exper Group. In: State of the Art Reviews and Related Papers—Center on Nanotechnology and Society. 2004 Conference. Published Jun. 14, 2004. p. 1-291. Available at http://www.nano-and-society.org/NELSI/documents/ECreviewsandpapers061404.pdf. Accessed Jan. 11, 2009.
(Continued)

*Primary Examiner* — Duc Nguyen
*Assistant Examiner* — Phan Le
(74) *Attorney, Agent, or Firm* — Levine Bagade Han LLP

(57) ABSTRACT

Various methods and apparatus for processing audio signals are disclosed herein. The assembly may be attached, adhered, or otherwise embedded into or upon a removable oral appliance to form a hearing aid assembly. Such an oral appliance may be a custom-made device which can enhance and/or optimize received audio signals for vibrational conduction to the user. Received audio signals may be processed to cancel acoustic echo such that undesired sounds received by one or more intra-buccal and/or extra-buccal microphones are eliminated or mitigated. Additionally, a multiband actuation system may be used where two or more transducers each deliver sounds within certain frequencies. Also, the assembly may also utilize the sensation of directionality via the conducted vibrations to emulate directional perception of audio signals received by the user. Another feature may include the ability to vibrationally conduct ancillary audio signals to the user along with primary audio signals.

30 Claims, 19 Drawing Sheets

(51) Int. Cl.
*H04R 1/46* (2006.01)
*A61C 5/00* (2006.01)
*A61C 8/00* (2006.01)
*H04R 3/04* (2006.01)

(52) U.S. Cl.
CPC ............ *H04R 25/606* (2013.01); *H04R 25/602* (2013.01); *H04R 25/604* (2013.01); *H04R 2225/67* (2013.01); *H04R 2420/07* (2013.01); *H04R 2460/13* (2013.01)

(56) References Cited

U.S. PATENT DOCUMENTS

| | | | |
|---|---|---|---|
| 2,230,397 A | 2/1941 | Abraham | |
| 2,242,118 A | 5/1941 | Fischer | |
| 2,318,872 A | 5/1943 | Madiera | |
| 2,977,425 A | 3/1961 | Cole | |
| 2,995,633 A | 8/1961 | Puharich et al. | |
| 3,156,787 A | 11/1964 | Puharich et al. | |
| 3,170,993 A | 2/1965 | Puharich et al. | |
| 3,267,931 A | 8/1966 | Puharich et al. | |
| 3,325,743 A | 6/1967 | Blum | |
| 3,712,962 A | 1/1973 | Epley | |
| 3,787,641 A | 1/1974 | Santori | |
| 3,894,196 A | 7/1975 | Briskey | |
| 3,985,977 A | 10/1976 | Beaty et al. | |
| 4,025,732 A | 5/1977 | Traunmuller | |
| 4,150,262 A | 4/1979 | Ono | |
| 4,498,461 A | 2/1985 | Hakansson | |
| 4,591,668 A | 5/1986 | Iwata | |
| 4,612,915 A | 9/1986 | Hough et al. | |
| 4,642,769 A | 2/1987 | Petrofsky | |
| 4,738,268 A | 4/1988 | Kipnis | |
| 4,791,673 A | 12/1988 | Schreiber | |
| 4,817,044 A | 3/1989 | Ogren | |
| 4,832,033 A | 5/1989 | Maher et al. | |
| 4,904,233 A | 2/1990 | Haakansson et al. | |
| 4,920,984 A | 5/1990 | Furumichi et al. | |
| 4,962,559 A | 10/1990 | Schuman | |
| 4,982,434 A | 1/1991 | Lenhardt et al. | |
| 5,012,520 A | 4/1991 | Steeger | |
| 5,033,999 A | 7/1991 | Mersky | |
| 5,047,994 A | 9/1991 | Lenhardt et al. | |
| 5,060,526 A | 10/1991 | Barth et al. | |
| 5,082,007 A | 1/1992 | Adell | |
| 5,233,987 A | 8/1993 | Fabian et al. | |
| 5,323,468 A | 6/1994 | Bottesch | |
| 5,325,436 A | 6/1994 | Soli et al. | |
| 5,354,326 A | 10/1994 | Comben et al. | |
| 5,372,142 A | 12/1994 | Madsen et al. | |
| 5,402,496 A | 3/1995 | Soli et al. | |
| 5,403,262 A | 4/1995 | Gooch | |
| 5,447,489 A | 9/1995 | Issalene et al. | |
| 5,455,842 A | 10/1995 | Merskey et al. | |
| 5,460,593 A | 10/1995 | Mersky et al. | |
| 5,477,489 A | 12/1995 | Wiedmann | |
| 5,546,459 A | 8/1996 | Sih et al. | |
| 5,558,618 A | 9/1996 | Maniglia | |
| 5,565,759 A | 10/1996 | Dunstan | |
| 5,579,284 A | 11/1996 | May | |
| 5,616,027 A | 4/1997 | Jacobs et al. | |
| 5,624,376 A | 4/1997 | Ball et al. | |
| 5,661,813 A | 8/1997 | Shimauchi et al. | |
| 5,706,251 A | 1/1998 | May | |
| 5,760,692 A | 6/1998 | Block | |
| 5,793,875 A | 8/1998 | Lehr et al. | |
| 5,800,336 A * | 9/1998 | Ball et al. | 600/25 |
| 5,812,496 A | 9/1998 | Peck | |
| 5,828,765 A | 10/1998 | Gable | |
| 5,902,167 A | 5/1999 | Filo et al. | |
| 5,914,701 A | 6/1999 | Gersheneld et al. | |
| 5,961,443 A | 10/1999 | Rastatter et al. | |
| 5,984,681 A | 11/1999 | Huang | |
| 6,029,558 A | 2/2000 | Stevens et al. | |
| 6,047,074 A | 4/2000 | Zoels et al. | |
| 6,057,668 A | 5/2000 | Chao | |
| 6,068,590 A * | 5/2000 | Brisken | 600/25 |
| 6,072,884 A | 6/2000 | Kates | |
| 6,072,885 A | 6/2000 | Stockham, Jr. et al. | |
| 6,075,557 A | 6/2000 | Holliman et al. | |
| 6,115,477 A | 9/2000 | Filo et al. | |
| 6,118,882 A | 9/2000 | Haynes | |
| 6,171,229 B1 | 1/2001 | Kroll et al. | |
| 6,223,018 B1 | 4/2001 | Fukumoto et al. | |
| 6,239,705 B1 | 5/2001 | Glen | |
| 6,333,269 B2 | 12/2001 | Naito et al. | |
| 6,371,758 B1 | 4/2002 | Kittelsen | |
| 6,377,693 B1 | 4/2002 | Lippa et al. | |
| 6,394,969 B1 | 5/2002 | Lenhardt | |
| 6,504,942 B1 | 1/2003 | Hong et al. | |
| 6,533,747 B1 | 3/2003 | Polaschegg et al. | |
| 6,538,558 B2 | 3/2003 | Sakazume et al. | |
| 6,585,637 B2 | 7/2003 | Brillhart et al. | |
| 6,629,922 B1 | 10/2003 | Puria et al. | |
| 6,631,197 B1 | 10/2003 | Taenzer | |
| 6,633,747 B1 | 10/2003 | Reiss | |
| 6,658,124 B1 | 12/2003 | Meadows | |
| 6,682,472 B1 | 1/2004 | Davis | |
| 6,694,035 B1 | 2/2004 | Teicher et al. | |
| 6,754,472 B1 | 6/2004 | Williams et al. | |
| 6,778,674 B1 | 8/2004 | Panasik et al. | |
| 6,826,284 B1 | 11/2004 | Benesty et al. | |
| 6,885,753 B2 | 4/2005 | Bank | |
| 6,917,688 B2 | 7/2005 | Yu et al. | |
| 6,941,952 B1 | 9/2005 | Rush, III | |
| 6,954,668 B1 | 10/2005 | Cuozzo | |
| 6,985,599 B2 | 1/2006 | Asnes | |
| 7,003,099 B1 | 2/2006 | Zhang et al. | |
| 7,010,139 B1 | 3/2006 | Smeehuyzen | |
| 7,033,313 B2 | 4/2006 | Lupin et al. | |
| 7,035,415 B2 | 4/2006 | Belt et al. | |
| 7,074,222 B2 | 7/2006 | Westerkull | |
| 7,076,077 B2 | 7/2006 | Atsumi et al. | |
| 7,099,822 B2 | 8/2006 | Zangi | |
| 7,162,420 B2 | 1/2007 | Zangi et al. | |
| 7,171,003 B1 | 1/2007 | Venkatesh et al. | |
| 7,171,008 B2 | 1/2007 | Elko | |
| 7,174,022 B1 | 2/2007 | Zhang et al. | |
| 7,174,026 B2 | 2/2007 | Niederdränk | |
| 7,206,423 B1 | 4/2007 | Feng et al. | |
| 7,246,058 B2 | 7/2007 | Burnett | |
| 7,258,533 B2 | 8/2007 | Tanner et al. | |
| 7,269,266 B2 | 9/2007 | Anjanappa et al. | |
| 7,271,569 B2 | 9/2007 | Oglesbee | |
| 7,281,924 B2 | 10/2007 | Ellison | |
| 7,310,427 B2 | 12/2007 | Retchin et al. | |
| 7,329,226 B1 | 2/2008 | Ni et al. | |
| 7,331,349 B2 | 2/2008 | Brady et al. | |
| 7,333,624 B2 | 2/2008 | Husung | |
| 7,361,216 B2 | 4/2008 | Kangas et al. | |
| 7,409,070 B2 | 8/2008 | Pitulia | |
| 7,486,798 B2 | 2/2009 | Anjanappa et al. | |
| 7,512,448 B2 | 3/2009 | Malick et al. | |
| 7,520,851 B2 | 4/2009 | Davis et al. | |
| 7,522,738 B2 | 4/2009 | Miller, III | |
| 7,522,740 B2 | 4/2009 | Julstrom et al. | |
| 7,664,277 B2 | 2/2010 | Abolfathi et al. | |
| 7,724,911 B2 | 5/2010 | Menzel et al. | |
| 7,796,769 B2 | 9/2010 | Abolfathi | |
| 7,801,319 B2 | 9/2010 | Abolfathi | |
| 7,844,064 B2 | 11/2010 | Abolfathi et al. | |
| 7,844,070 B2 | 11/2010 | Abolfathi | |
| 7,876,906 B2 | 1/2011 | Abolfathi | |
| 8,254,611 B2 | 8/2012 | Abolfathi et al. | |
| 8,270,638 B2 | 9/2012 | Abolfathi et al. | |
| 8,588,447 B2 | 11/2013 | Abolfathi et al. | |
| 2001/0003788 A1 | 6/2001 | Ball et al. | |
| 2001/0051776 A1 | 12/2001 | Lenhardt | |
| 2002/0026091 A1 | 2/2002 | Leysieffer | |
| 2002/0039427 A1 | 4/2002 | Whitwell et al. | |
| 2002/0071581 A1 | 6/2002 | Leysieffer et al. | |
| 2002/0077831 A1 | 6/2002 | Numa | |
| 2002/0122563 A1 | 9/2002 | Schumaier | |
| 2002/0173697 A1 | 11/2002 | Lenhardt | |

(56) References Cited

U.S. PATENT DOCUMENTS

| | | |
|---|---|---|
| 2003/0048915 A1 | 3/2003 | Bank |
| 2003/0059078 A1 | 3/2003 | Downs et al. |
| 2003/0091200 A1 | 5/2003 | Pompei |
| 2003/0212319 A1 | 11/2003 | Magill |
| 2004/0057591 A1 | 3/2004 | Beck et al. |
| 2004/0063073 A1 | 4/2004 | Kajimoto et al. |
| 2004/0131200 A1 | 7/2004 | Davis |
| 2004/0141624 A1 | 7/2004 | Davis et al. |
| 2004/0202339 A1 | 10/2004 | O'Brien, Jr. et al. |
| 2004/0202344 A1 | 10/2004 | Anjanappa et al. |
| 2004/0214130 A1 | 10/2004 | Fischer et al. |
| 2004/0243481 A1 | 12/2004 | Bradbury et al. |
| 2004/0247143 A1 | 12/2004 | Lantrua et al. |
| 2005/0037312 A1 | 2/2005 | Uchida |
| 2005/0067816 A1 | 3/2005 | Buckman |
| 2005/0070782 A1 | 3/2005 | Brodkin |
| 2005/0129257 A1 | 6/2005 | Tamura |
| 2005/0189910 A1 | 9/2005 | Hui |
| 2005/0196008 A1* | 9/2005 | Anjanappa et al. ........... 381/380 |
| 2005/0241646 A1 | 11/2005 | Sotos et al. |
| 2006/0008106 A1 | 1/2006 | Harper |
| 2006/0025648 A1 | 2/2006 | Lupin et al. |
| 2006/0064037 A1 | 3/2006 | Shalon et al. |
| 2006/0167335 A1 | 7/2006 | Park et al. |
| 2006/0207611 A1 | 9/2006 | Anonsen |
| 2006/0270467 A1 | 11/2006 | Song et al. |
| 2006/0275739 A1 | 12/2006 | Ray |
| 2007/0010704 A1 | 1/2007 | Pitulia |
| 2007/0035917 A1 | 2/2007 | Hotelling et al. |
| 2007/0036370 A1 | 2/2007 | Granovetter et al. |
| 2007/0041595 A1 | 2/2007 | Carazo et al. |
| 2007/0105072 A1 | 5/2007 | Koljonen |
| 2007/0142072 A1 | 6/2007 | Lassally |
| 2007/0223735 A1 | 9/2007 | LoPresti et al. |
| 2007/0230713 A1 | 10/2007 | Davis |
| 2007/0242835 A1 | 10/2007 | Davis |
| 2007/0265533 A1 | 11/2007 | Tran |
| 2007/0276270 A1 | 11/2007 | Tran |
| 2007/0280491 A1 | 12/2007 | Abolfathi |
| 2007/0280492 A1 | 12/2007 | Abolfathi |
| 2007/0280493 A1 | 12/2007 | Abolfathi |
| 2007/0280495 A1 | 12/2007 | Abolfathi |
| 2007/0286440 A1 | 12/2007 | Abolfathi et al. |
| 2007/0291972 A1 | 12/2007 | Abolfathi et al. |
| 2008/0019542 A1 | 1/2008 | Menzel et al. |
| 2008/0019557 A1 | 1/2008 | Bevirt et al. |
| 2008/0021327 A1 | 1/2008 | El-Bialy et al. |
| 2008/0064993 A1 | 3/2008 | Abolfathi et al. |
| 2008/0070181 A1 | 3/2008 | Abolfathi et al. |
| 2008/0109972 A1 | 5/2008 | Mah et al. |
| 2008/0205678 A1 | 8/2008 | Boglavskij et al. |
| 2008/0304677 A1 | 12/2008 | Abolfathi et al. |
| 2009/0028352 A1 | 1/2009 | Petroff |
| 2009/0052698 A1 | 2/2009 | Rader et al. |
| 2009/0088598 A1 | 4/2009 | Abolfathi |
| 2009/0097684 A1 | 4/2009 | Abolfathi et al. |
| 2009/0097685 A1 | 4/2009 | Menzel et al. |
| 2009/0099408 A1 | 4/2009 | Abolfathi et al. |
| 2009/0105523 A1 | 4/2009 | Kassayan et al. |
| 2009/0147976 A1 | 6/2009 | Abolfathi |
| 2009/0149722 A1 | 6/2009 | Abolfathi et al. |
| 2009/0180652 A1 | 7/2009 | Davis et al. |
| 2009/0220115 A1 | 9/2009 | Lantrua |
| 2009/0226020 A1 | 9/2009 | Abolfathi |
| 2010/0189288 A1 | 7/2010 | Menzel et al. |
| 2010/0220883 A1 | 9/2010 | Menzel et al. |
| 2010/0312568 A1 | 12/2010 | Abolfathi |
| 2010/0322449 A1 | 12/2010 | Abolfathi |
| 2011/0002492 A1 | 1/2011 | Abolfathi et al. |
| 2011/0026740 A1 | 2/2011 | Abolfathi |
| 2011/0116659 A1 | 5/2011 | Abolfathi |
| 2013/0003996 A1 | 1/2013 | Menzel et al. |
| 2013/0010987 A1 | 1/2013 | Abolfathi et al. |

FOREIGN PATENT DOCUMENTS

| | | |
|---|---|---|
| EP | 1783919 A1 | 5/2007 |
| GB | 1066299 A | 4/1967 |
| JP | 56-026490 | 3/1981 |
| JP | 2007028248 A2 | 2/2007 |
| JP | 2007028610 A2 | 2/2007 |
| JP | 2007044284 A2 | 2/2007 |
| JP | 2007049599 A2 | 2/2007 |
| JP | 2007049658 A2 | 2/2007 |
| WO | WO 83/02047 | 6/1983 |
| WO | WO 91/02678 | 3/1991 |
| WO | WO 95/06398 | 3/1995 |
| WO | WO 95/19678 | 7/1995 |
| WO | WO 96/21335 | 7/1996 |
| WO | WO 02/09622 | 2/2002 |
| WO | WO 03/001845 | 1/2003 |
| WO | WO 2004/045242 | 5/2004 |
| WO | WO 2004/093493 | 10/2004 |
| WO | WO 2004/105650 | 12/2004 |
| WO | WO 2005/000391 | 1/2005 |
| WO | WO 2005/037153 | 4/2005 |
| WO | WO 2005/053533 | 6/2005 |
| WO | WO 2006/044161 | 4/2006 |
| WO | WO 2006/088410 | 8/2006 |
| WO | WO 2006/130909 | 12/2006 |
| WO | WO 2007/043055 | 4/2007 |
| WO | WO 2007/052251 | 5/2007 |
| WO | WO 2007/059185 | 5/2007 |
| WO | WO 2007/140367 | 12/2007 |
| WO | WO 2007/140368 | 12/2007 |
| WO | WO 2007/140373 | 12/2007 |
| WO | WO 2007/143453 | 12/2007 |
| WO | WO 2008/024794 | 2/2008 |
| WO | WO 2008/030725 | 3/2008 |
| WO | WO 2009/014812 | 1/2009 |
| WO | WO 2009/025917 | 2/2009 |
| WO | WO 2009/066296 | 5/2009 |
| WO | WO 2009/102889 | 8/2009 |
| WO | WO 2009/111404 | 9/2009 |
| WO | WO 2009/111566 | 9/2009 |

OTHER PUBLICATIONS

Berard, G., "Hearing Equals Behavior" [summary], 1993, http://www.bixby.org/faq/tinnitus/treatment.html.

Bozkaya, D. et al., "Mechanics of the Tapered Interference Fit in Dental Implants." published Oct. 2002 [online], retrieved Oct. 14, 2010, http://www1.coe.neu.edu/~smuftu/Papers/paper-interference-fit-elsevier-2.pdf.

Broyhill, D., "Battlefield Medical Information System—Telemedicine," A research paper presented to the U.S. Army Command and General Staff College in partial Fulfillment of the requirements for A462 Combat Health Support Seminar, 12 pages, 2003.

Dental Cements—Premarket Notification, U.S. Department of Health and Human Services Food and Drug Administration Center for Devices and Radiological Health, pp. 1-10, Aug. 18, 1998.

Henry, et al. "Comparison of Custom Sounds for Achieving Tinnitus Relief," *J Am Acad Audiol*,15:585-598, 2004.

Jastreboff, Pawel, J., "Phantom auditory perception (tinnitus): mechanisms of generation and perception," *Nueroscience Research*, 221-254, 1990, Elsevier Scientific Publishers Irelland, Ltd.

Robb, "Tinnitus Device Directory Part I," *Tinnitus Today*, p. 22, Jun. 2003.

Song, S. et al., "A 0.2-mW 2-Mb/s Digital Transceiver Based on Wideband Signaling for Human Body Communications," *IEEE J Solid-State Cir*, 42(9), 2021-2033, Sep. 2007.

Stuart, A., et al., "Investigation of the Impact of Altered Auditory Feedback In-The-Ear Devices on the Speech of People Who Stutter: Initial Fitting and 4-Month Follow-Up," *Int J Lang Commun Disord*, 39(1), Jan. 2004, [abstract only].

Wen, Y. et al, "Online Prediction of Battery Lifetime for Embedded and Mobile Devices," Special Issue on Embedded Systems: Springer-Verlag Heidelberg Lecture Notes in Computer Sciece, V3164/2004, 15 pages, Dec. 2004.

* cited by examiner

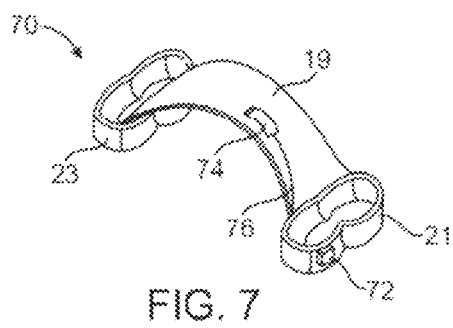
FIG. 7
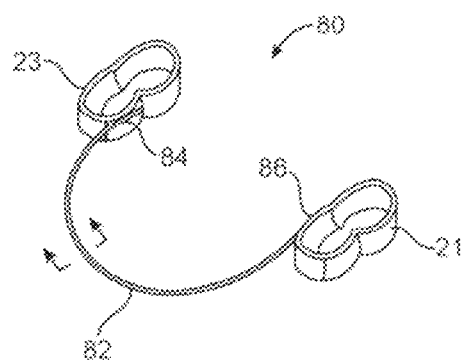
FIG. 8A
   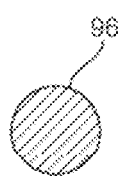
FIG. 8B    FIG. 8C    FIG. 8D    FIG. 8E

METHODS AND APPARATUS FOR PROCESSING AUDIO SIGNALS

CROSS-REFERENCE TO RELATED APPLICATIONS

This application is a continuation of U.S. patent application Ser. No. 12/862,933 filed Aug. 25, 2010, which is a continuation of U.S. patent application Ser. No. 11/672,271 filed Feb. 7, 2007 (now U.S. Pat. No. 7,801,319 issued Sep. 21, 2010), which claims the benefit of priority to U.S. Prov. Pat. App. Ser. Nos. 60/809,244 tiled May 30, 2006 and 60/820,223 filed Jul. 24, 2006, each of which are incorporated herein by reference in their entirety.

FIELD OF THE INVENTION

The present invention relates to methods and apparatus for processing and/or enhancing audio signals for transmitting these signals as vibrations through teeth or bone structures in and/or around a mouth. More particularly, the present invention relates to methods and apparatus for receiving audio signals and processing them to enhance its quality and/or to emulate various auditory features for transmitting these signals via sound conduction through teeth or bone structures in and/or around the mouth such that the transmitted signals correlate to auditory signals received by a user.

BACKGROUND OF THE INVENTION

Hearing loss affects over 31 million people in the United States (about 13% of the population). As a chronic condition, the incidence of hearing impairment rivals that of heart disease and, like heart disease, the incidence of hearing, impairment increases sharply with age.

While the vast majority of those with hearing loss can be helped by a well-fitted, high quality hearing device, only 22% of the total hearing impaired population own hearing devices. Current products and distribution methods are not able to satisfy or reach over 20 million persons with hearing impairment in the U.S. alone.

Hearing loss adversely affects a person's quality of life and psychological well-being. Individuals with hearing impairment often withdraw from social interactions to avoid frustrations resulting from inability to understand conversations. Recent studies have shown that hearing impairment causes increased stress levels, reduced self-confidence, reduced sociability and reduced effectiveness in the workplace.

The human ear generally comprises three regions: the outer ear, the middle ear, and the inner ear. The outer ear generally comprises the external auricle and the ear canal, which is a tubular pathway through which sound reaches the middle ear. The outer ear is separated from the middle ear by the tympanic membrane (eardrum). The middle ear generally comprises three small bones, known as the ossicles, which form a mechanical conductor from the tympanic membrane to the inner ear. Finally, the inner ear includes the cochlea, which is a fluid-filled structure that contains a large number of delicate sensory hair cells that are connected to the auditory nerve.

Hearing loss can also be classified in terms of being conductive, sensorineural, or a combination of both. Conductive hearing impairment typically results from diseases or disorders that limit the transmission of sound through the middle ear. Most conductive impairments can be treated medically or surgically. Purely conductive hearing loss represents a relatively small portion of the total hearing impaired population (estimated at less than 5% of the total hearing impaired population).

Sensorineural hearing losses occur mostly in the inner ear and account for the vast majority of hearing impairment (estimated at 90-95% of the total hearing impaired population). Sensorineural hearing impairment (sometimes called "nerve loss") is largely caused by damage to the sensory hair cells inside the cochlea. Sensorineural hearing impairment occurs naturally as a result of aging or prolonged exposure to loud music and noise. This type of hearing loss cannot be reversed nor can it be medically or surgically treated; however, the use of properly fitted hearing devices can improve the individual's quality of life.

Conventional hearing devices are the most common devices used to treat mild to severe sensorineural hearing impairment. These are acoustic devices that amplify sound to the tympanic membrane. These devices are individually customizable to the patient's physical and acoustical characteristics over four to six separate visits to an audiologist or hearing instrument specialist. Such devices generally comprise a microphone, amplifier, battery, and speaker. Recently, hearing device manufacturers have increased the sophistication of sound processing, often using digital technology, to provide features such as programmability and multi-band compression. Although these devices have been miniaturized and are less obtrusive, they are still visible and have major acoustic limitation.

Industry research has shown that the primary obstacles for not purchasing a hearing device generally include: a) the stigma associated with wearing a hearing device; b) dissenting attitudes on the part of the medical profession, particularly ENT physicians; c) product value issues related to perceived performance problems; d) general lack of information and education at the consumer and physician level; and e) negative word-of-mouth from dissatisfied users.

Other devices such as cochlear implants have been developed for people who have severe to profound hearing loss and are essentially deaf (approximately 2% of the total hearing impaired population). The electrode of a cochlear implant is inserted into the inner ear in an invasive and non-reversible surgery. The electrode electrically stimulates the auditory nerve through an electrode array that provides audible cues to the user, which are not usually interpreted by the brain as normal sound. Users generally require intensive and extended counseling and training following surgery to achieve the expected benefit.

Other devices such as electronic middle ear implants generally are surgically placed within the middle ear of the hearing impaired. They are surgically implanted devices with an externally worn component.

The manufacture, fitting and dispensing of hearing devices remain an arcane and inefficient process. Most hearing devices are custom manufactured, fabricated by the manufacturer to fit the ear of each prospective purchaser. An impression of the ear canal is taken by the dispenser (either an audiologist or licensed hearing instrument specialist) and mailed to the manufacturer for interpretation and fabrication of the custom molded rigid plastic casing. Hand-wired electronics and transducers (microphone and speaker) are then placed inside the casing, and the final product is shipped back to the dispensing professional after some period of time, typically one to two weeks.

The time cycle for dispensing a hearing device, from the first diagnostic session to the final fine-tuning session, typically spans a period over several weeks, such as six to eight weeks, and involves multiple with the dispenser.

Moreover, typical hearing aid devices fail to eliminate background noises or fail to distinguish between background noise and desired sounds. Accordingly, there exists a need for methods and apparatus for receiving audio signals and processing them to enhance its quality and/or to emulate various auditory features for transmitting these signals via sound conduction through teeth or bone structures in and/or around the mouth for facilitating the treatment of hearing loss in patients.

SUMMARY OF THE INVENTION

An electronic and transducer device may be attached, adhered, or otherwise embedded into or upon a removable dental or oral appliance to form a hearing aid assembly. Such a removable oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

The assembly for transmitting vibrations via at least one tooth may generally comprise a housing having a shape which is conformable to at least a portion of the at least one tooth, and an actuatable transducer disposed within or upon the housing and in vibratory communication with a surface of the at least one tooth. Moreover, the transducer itself may be a separate assembly from the electronics and may be positioned along another surface of the tooth, such as the occlusal surface, or even attached to an implanted post or screw embedded into the underlying bone.

In receiving and processing the various audio signals typically received by a user, various configurations of the oral appliance and processing of the received audio signals may be utilized to enhance and/or optimize the conducted vibrations which are transmitted to the user. For instance, in configurations where one or more microphones are positioned within the user's mouth, filtering features such as Acoustic Echo Cancellation (AEC) may be optionally utilized to eliminate or mitigate undesired sounds received by the microphones. In such a configuration, at least two intra-buccal microphones may be utilized to separate out desired sounds (e.g., sounds received from outside the body such as speech, music, etc.) from undesirable sounds (e.g., sounds resulting from chewing, swallowing, breathing, self-speech, teeth grinding, etc.).

If these undesirable sounds are not filtered or cancelled, they may be amplified along with the desired audio signals making for potentially unintelligible audio quality for the user. Additionally, desired audio sounds may be generally received at relatively lower sound pressure levels because such signals are more likely to be generated at a distance from the user and may have to pass through the cheek of the user while the undesired sounds are more likely to be generated locally within the oral cavity of the user. Samples of the undesired sounds may be compared against desired sounds to eliminate or mitigate the undesired sounds prior to actuating the one or more transducers to vibrate only the resulting desired sounds to the user.

Independent from or in combination with acoustic echo cancellation, another processing feature for the oral appliance may include use of a multiband actuation system to facilitate the efficiency with which audio signals may be conducted to the user. Rather than utilizing a single transducer to cover the entire range of the frequency spectrum (e.g., 200 Hz to 10,000 Hz), one variation may utilize two or more transducers where each transducer is utilized to deliver sounds within certain frequencies. For instance, a first transducer may be utilized to deliver sounds in the 200 Hz to 2000 Hz frequency range and a second transducer may be used to deliver sounds in the 2000 Hz to 10,000 Hz frequency range. Alternatively, these frequency ranges may be discrete or overlapping. As individual transducers may be configured to handle only a subset of the frequency spectrum, the transducers may be more efficient in their design.

Yet another process which may utilize the multiple transducers may include the utilization of directionality via the conducted vibrations to emulate the directional perception of audio signals received by the user. In one example for providing the perception of directionality with an oral appliance, two or more transducers may be positioned apart from one another along respective retaining portions. One transducer may be actuated corresponding to an audio signal while the other transducer may be actuated corresponding to the same audio signal but with a phase and/or amplitude and/or delay difference intentionally induced corresponding to a direction emulated for the user. Generally, upon receiving a directional audio signal and depending upon the direction to be emulated and the separation between the respective transducers, a particular phase and/or gain and/or delay change to the audio signal may be applied to the respective transducer while leaving the other transducer to receive the audio signal unchanged.

Another feature which may utilize the oral appliance and processing capabilities may include the ability to vibrationally conduct ancillary audio signals to the user, e.g., the oral appliance may be configured to wirelessly receive and conduct signals from secondary audio sources to the user. Examples may include the transmission of an alarm signal which only the user may hear or music conducted to the user in public locations, etc. The user may thus enjoy privacy in receiving these ancillary signals while also being able to listen and/or converse in an environment where a primary audio signal is desired.

BRIEF DESCRIPTION OF THE DRAWINGS

FIG. 7 illustrates another variation of a removable oral appliance supported by an arch and having a microphone unit integrated within the arch.

FIG. 8A illustrates another variation of the removable oral appliance supported by a connecting member which may be positioned along the lingual or buccal surfaces of a patient's row of teeth.

FIGS. 8B to 8E show examples of various cross-sections of the connecting support member of the appliance of FIG. 8A.

DETAILED DESCRIPTION OF THE INVENTION

An electronic and transducer device may be attached, adhered, or otherwise embedded into or upon a removable oral appliance or other oral device to form a hearing aid assembly. Such an oral appliance may be a custom-made device fabricated from a thermal forming process utilizing a replicate model of a dental structure obtained by conventional dental impression methods. The electronic and transducer assembly may receive incoming sounds either directly or through a receiver to process and amplify the signals and transmit the processed sounds via a vibrating transducer element coupled to a tooth or other bone structure, such as the maxillary, mandibular, or palatine bone structure.

Figure 1:
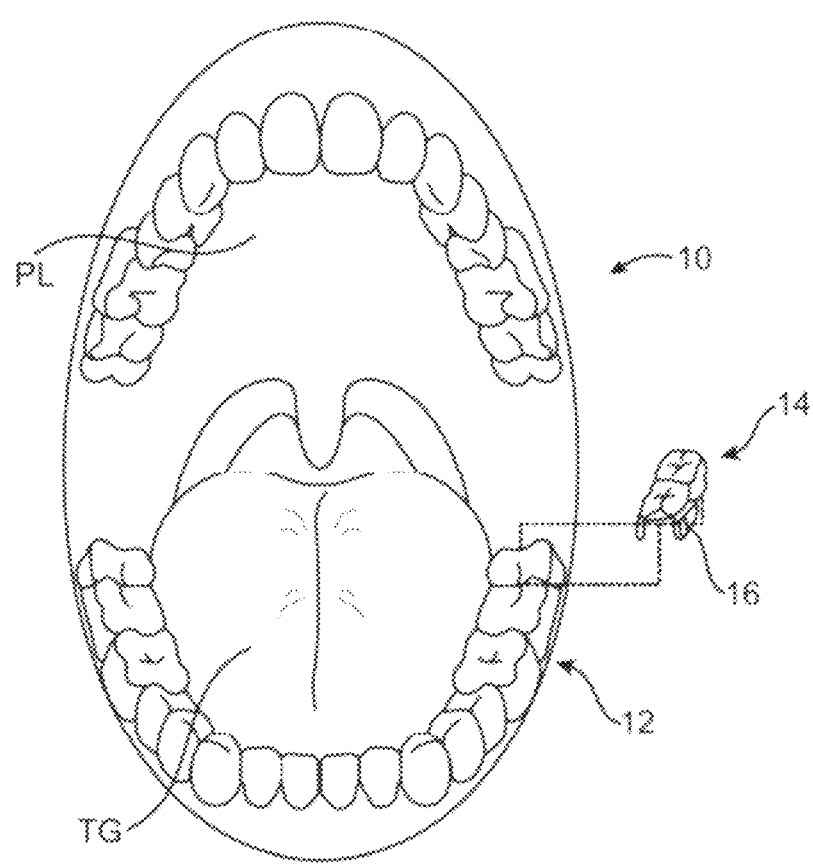
FIG. 1 illustrates the dentition of a patient's teeth and one variation of a hearing aid device which is removably placed upon or against the patient's tooth or teeth as a removable oral appliance.

As shown in FIG. 1, a patient's mouth and dentition 10 is illustrated showing one possible location for removably attaching hearing aid assembly 14 upon or against at least one tooth, such as a molar 12. The patient's tongue TG and palate PL are also illustrated for reference. An electronics and/or transducer assembly 16 may be attached, adhered, or otherwise embedded into or upon the assembly 14, as described below in further detail.

Figure 2A:
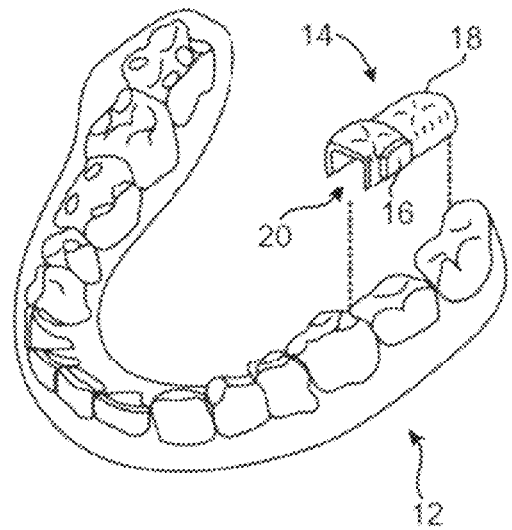
FIG. 2A illustrates a perspective view of the lower teeth showing one exemplary location for placement of the removable oral appliance hearing aid device.

FIG. 2A shows a perspective view of the patient's lower dentition illustrating the hearing aid assembly 14 comprising a removable oral appliance 18 and the electronics and/or transducer assembly 16 positioned along a side surface of the assembly 14. In this variation, oral appliance 18 may be fitted upon two molars 12 within tooth engaging channel 20 defined by oral appliance 18 for stability upon the patient's teeth, although in other variations, a single molar or tooth may be utilized. Alternatively, more than two molars may be utilized for the oral appliance 18 to be attached upon or over. Moreover, electronics and/or transducer assembly 16 is shown positioned upon a side surface of oral appliance 18 such that the assembly 16 is aligned along a buccal surface of the tooth 12; however, other surfaces such as the lingual surface of the tooth 12 and other positions may also be utilized. The figures are illustrative of variations and are not intended to be limiting; accordingly, other configurations and shapes for oral appliance 18 are intended to be included herein.

Figure 2B:
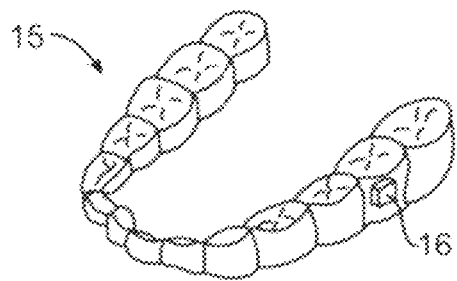
FIG. 2B illustrates another variation of the removable oral appliance in the form of an appliance which is placed over an entire row of teeth in the manner of a mouthguard.

FIG. 2B shows another variation of a removable oral appliance in the form of an appliance 15 which is placed over an entire row of teeth in the manner of a mouthguard. In this variation, appliance 15 may be configured to cover an entire bottom row of teeth or alternatively an entire upper row of teeth. In additional variations, rather than covering the entire rows of teeth, a majority of the row of teeth may be instead be covered by appliance 15. Assembly 16 may be positioned along one or more portions of the oral appliance 15.

Figure 2C:
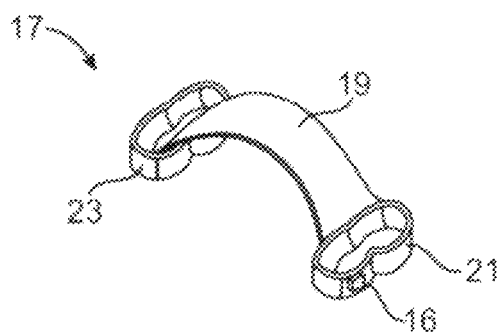
FIG. 2C illustrates another variation of the removable oral appliance which is supported by an arch.

FIG. 2C shows yet another variation of an oral appliance 17 having an arched configuration. In this appliance, one or more tooth retaining portions 21, 23, which in this variation may be placed along the upper row of teeth, may be supported by an arch 19 which may lie adjacent or along the palate of the user. As shown, electronics and/or transducer assembly 16 may be positioned along one or more portions of the tooth retaining portions 21, 23. Moreover, although the variation shown illustrates an arch 19 which may cover only a portion of the palate of the user, other variations may be configured to have an arch which covers the entire palate of the user.

Figure 2D:
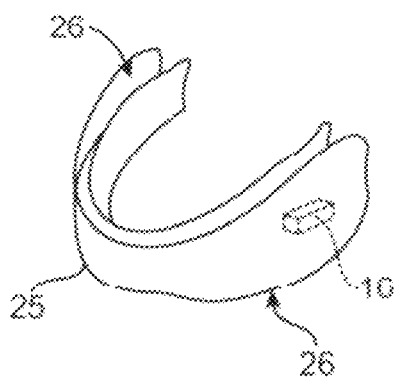
FIG. 2D illustrates another variation of an oral appliance configured as a mouthguard.

FIG. 2D illustrates yet another variation of an oral appliance in the form of a mouthguard or retainer 25 which may be inserted and removed easily from the user's mouth. Such a mouthguard or retainer 25 may be used in sports where conventional mouthguards are worn; however, mouthguard or retainer 25 having assembly 16 integrated therein may be utilized by persons, hearing impaired or otherwise, who may simply hold the mouthguard or retainer 25 via grooves or channels 26 between their teeth for receiving instructions remotely and communicating over a distance.

Generally, the volume of electronics and/or transducer assembly 16 may be minimized so as to be unobtrusive and as comfortable to the user when placed in the mouth. Although the size may be varied, a volume of assembly 16 may be less than 800 cubic millimeters. This volume is, of course, illustrative and not limiting as size and volume of assembly 16 and may be varied accordingly between different users.

Moreover, removable oral appliance 18 may be fabricated from various polymeric or a combination of polymeric and metallic materials using any number of methods, such as computer-aided machining processes using computer numerical control (CNC) systems or three-dimensional printing processes, e.g., stereolithography apparatus (SLA), selective laser sintering (SLS), and/or other similar processes utilizing three-dimensional geometry of the patient's dentition, which may be obtained via any number of techniques. Such techniques may include use of scanned dentition using intra-oral scanners such as laser, white light, ultrasound, mechanical three-dimensional touch scanners, magnetic resonance imaging (MRI), computed tomography (CT), other optical methods, etc.

In forming the removable oral appliance 18, the appliance 18 may be optionally formed such that it is molded to fit over the dentition and at least a portion of the adjacent gingival tissue to inhibit the entry of food, fluids, and other debris into the oral appliance 18 and between the transducer assembly and tooth surface. Moreover, the greater surface area of the oral appliance 18 may facilitate the placement and configuration of the assembly 16 onto the appliance 18.

Additionally, the removable oral appliance 18 may be optionally fabricated to have a shrinkage factor such that when placed onto the dentition, oral appliance 18 may be configured to securely grab onto the tooth or teeth as the appliance 18 may have a resulting size slightly smaller than the scanned tooth or teeth upon which the appliance 18 was formed. The fitting may result in a secure interference fit between the appliance 18 and underlying dentition.

Figure 3:
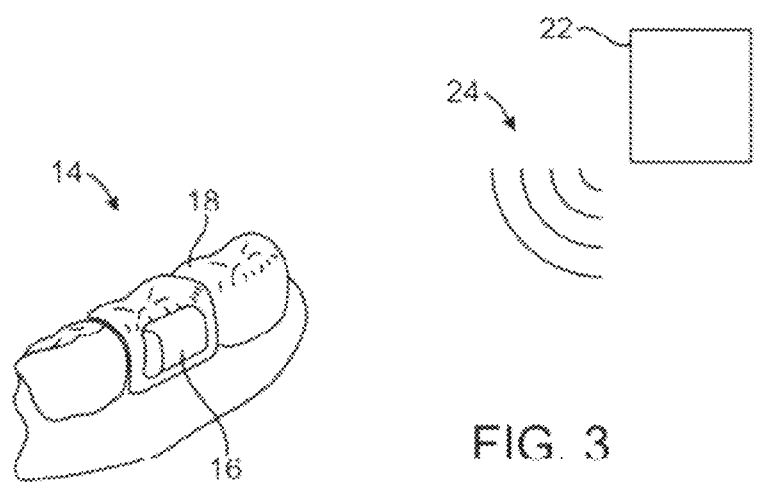
FIG. 3 illustrates a detail perspective view of the oral appliance positioned upon the patient's teeth utilizable in combination with a transmitting assembly external to the mouth and wearable by the patient in another variation of the device.

In one variation, with assembly 14 positioned upon the teeth, as shown in FIG. 3, an extra-buccal transmitter assembly 22 located outside the patient's mouth may be utilized to receive auditory signals for processing and transmission via a wireless signal 24 to the electronics and/or transducer assembly 16 positioned within the patient's mouth, which may then process and transmit the processed auditory signals via vibratory conductance to the underlying tooth and consequently to the patient's inner ear.

The transmitter assembly 22, as described in further detail below, may contain a microphone assembly as well as a transmitter assembly and may be configured in any number of shapes and forms worn by the user, such as a watch, necklace, lapel, phone, belt-mounted device, etc.

Figure 4:
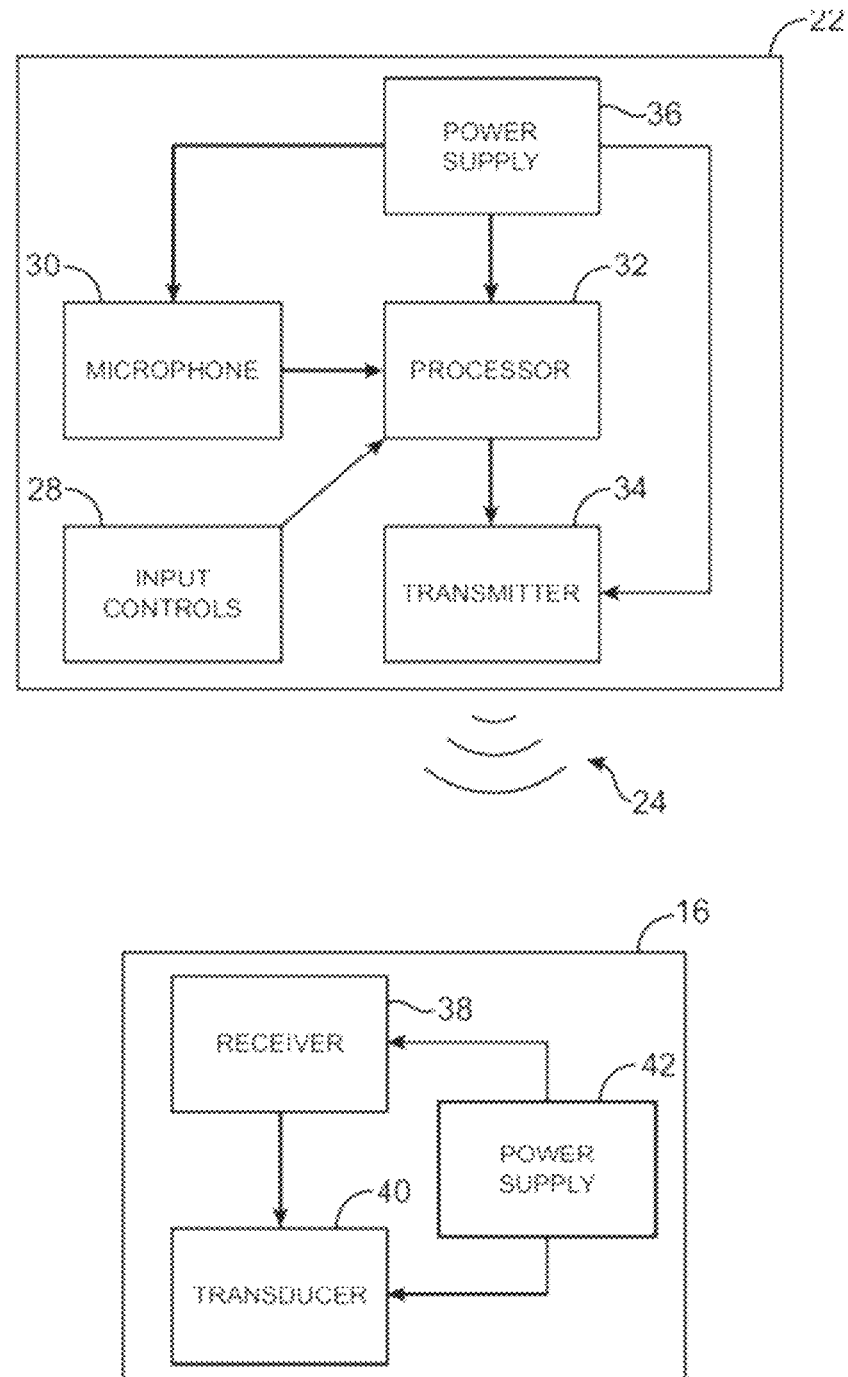
FIG. 4 shows an illustrative configuration of one variation of the individual components of the oral appliance device having an external transmitting assembly with a receiving and transducer assembly within the mouth.

FIG. 4 illustrates a schematic representation of one variation of hearing aid assembly 14 utilizing an extra-buccal transmitter assembly 22, which may generally comprise microphone or microphone array 30 (referred to "microphone 30" for simplicity) for receiving sounds and which is electrically connected to processor 32 for processing the auditory signals. Processor 32 may be connected electrically to transmitter 34 for transmitting the processed signals to the electronics and/or transducer assembly 16 disposed upon or adjacent to the user's teeth. The microphone 30 and processor 32 may be configured to detect and process auditory signals in any practicable range, but may be configured in one variation to detect auditory signals ranging, from, e.g., 250 Hertz to 20,000 Hertz.

With respect to microphone 30, a variety of various microphone systems may be utilized. For instance, microphone 30 may be a digital, analog, and/or directional type microphone. Such various types of microphones may be interchangeably configured to be utilized with the assembly, if so desired. Moreover, various configurations and methods for utilizing multiple microphones within the user's mouth may also be utilized, as further described below.

Power supply 36 may be connected to each of the components in transmitter assembly 22 to provide power thereto. The transmitter signals 24 may be in any wireless form utilizing, e.g., radio frequency, ultrasound, microwave, Blue Tooth® (BLUETOOTH SIG, INC., Bellevue, Wash.), etc. for transmission to assembly 16. Assembly 22 may also optionally include one or more input controls 28 that a user may manipulate to adjust various acoustic parameters of the electronics and/or transducer assembly 16, such as acoustic focusing, volume control, filtration, muting, frequency optimization, sound adjustments, and tone adjustments, etc.

The signals transmitted 24 by transmitter 34 may be received by electronics and/or transducer assembly 16 via receiver 38, which may be connected to an internal processor for additional processing of the received signals. The received signals may be communicated to transducer 40, which may vibrate correspondingly against a surface of the tooth to conduct the vibratory signals through the tooth and bone and subsequently to the middle ear to facilitate hearing of the user. Transducer 40 may be configured as any number of different vibratory mechanisms. For instance, in one variation, transducer 40 may be an electromagnetically actuated transducer. In other variations, transducer 40 may be in the form of a piezoelectric crystal having a range of vibratory frequencies, e.g., between 250 to 4000 kHz.

Power supply 42 may also be included with assembly 16 to provide power to the receiver, transducer, and/or processor, if also included. Although power supply 42 may be a simple battery, replaceable or permanent, other variations may include a power supply 42 which is charged by inductance via an external charger. Additionally, power supply 42 may alternatively be charged via direct coupling to an alternating current (AC) or direct current (DC) source. Other variations may include a power supply 42 which is charged via a mechanical mechanism, such as an internal pendulum or slidable electrical inductance charger as known in the art, which is actuated via, e.g., motions of the jaw and/or movement for translating the mechanical motion into stored electrical energy for charging power supply 42.

Figure 5:
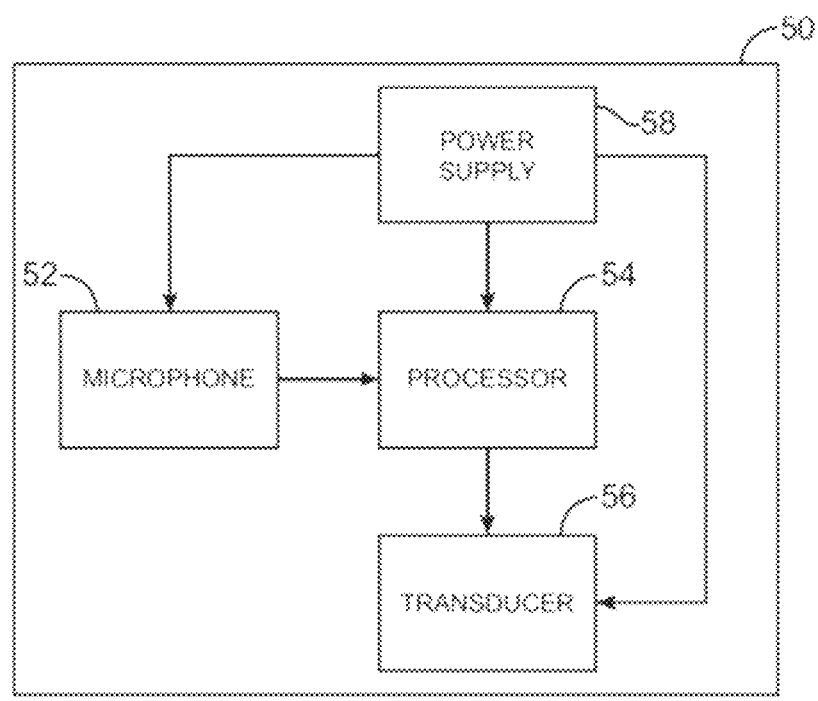
FIG. 5 shows an illustrative configuration of another variation of the device in which the entire assembly is contained by the oral appliance within the user's mouth.

In another variation of assembly 16, rather than utilizing an extra-buccal transmitter, hearing aid assembly 50 may be configured as an independent assembly contained entirely within the user's mouth, as shown in FIG. 5. Accordingly, assembly 50 may include at least one internal microphone 52 in communication with an on-board processor 54. Internal microphone 52 may comprise any number of different types of microphones, as described below in further detail. At least one processor 54 may be used to process any received auditory signals for filtering and/or amplifying the signals and transmitting them to transducer 56, which is in vibratory contact against the tooth surface. Power supply 58, as described above, may also be included within assembly 50 for providing power to each of the components of assembly 50 as necessary.

In order to transmit the vibrations corresponding to the received auditory signals efficiently and with minimal loss to the tooth or teeth, secure mechanical contact between the transducer and the tooth is ideally maintained to ensure efficient vibratory communication. Accordingly, any number of mechanisms may be utilized to maintain this vibratory communication.

Figure 6:
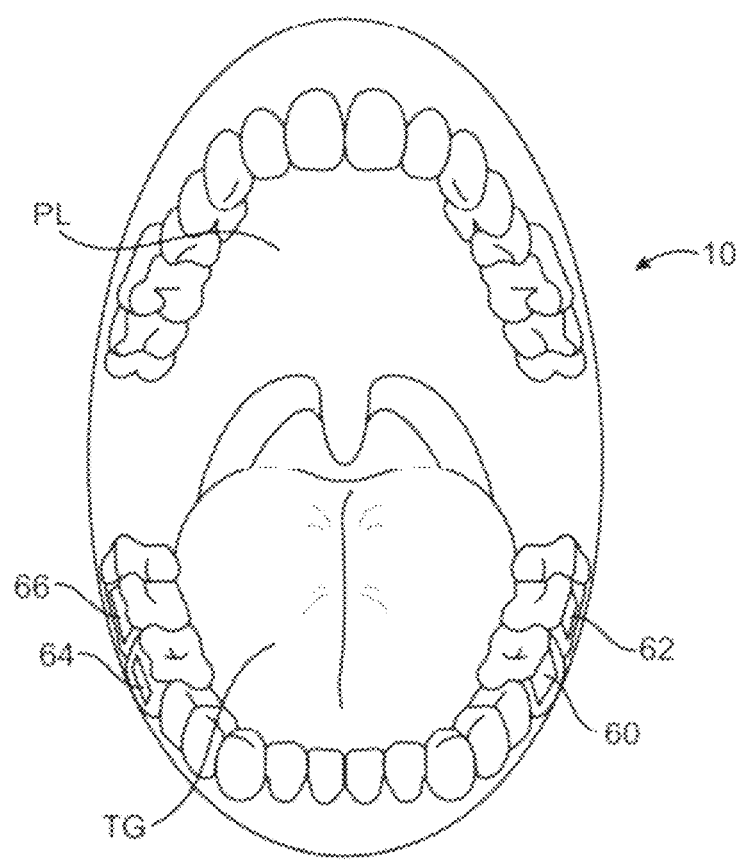
FIG. 6 illustrates an example of how multiple oral appliance hearing aid assemblies or transducers may be placed on multiple teeth throughout the patient's mouth.

For any of the variations described above, they may be utilized as a single device or in combination with any other variation herein, as practicable, to achieve the desired hearing level in the user. Moreover, more than one oral appliance device and electronics and/or transducer assemblies may be utilized at any one time. For example, FIG. 6 illustrates one example where multiple transducer assemblies 60, 62, 64, 66 may be placed on multiple teeth. Although shown on the lower row of teeth, multiple assemblies may alternatively be positioned and located along the upper row of teeth or both rows as well. Moreover, each of the assemblies may be configured to transmit vibrations within a uniform frequency range. Alternatively in other variations, different assemblies may be configured to vibrate within overlapping or non-overlapping frequency ranges between each assembly. As mentioned above, each transducer 60, 62, 64, 66 can be programmed or preset for a different frequency response such that each transducer may be optimized for a different frequency response and/or transmission to deliver a relatively high-fidelity sound to the user.

Moreover, each of the different transducers 60, 62, 64, 66 can also be programmed to vibrate in a manner which indicates the directionality of sound received by the microphone worn by the user. For example, different transducers positioned at different locations within the user's mouth can vibrate in a specified manner by providing sound or vibrational queues to inform the user which direction a sound was detected relative to an orientation of the user, as described in further detail below. For instance, a first transducer located, e.g., on a user's left tooth, can be programmed to vibrate for sound detected originating from the user's left side. Similarly, a second transducer located, e.g., on a user's right tooth, can be programmed to vibrate for sound detected originating from the user's right side. Other variations and queues may be utilized as these examples are intended to be illustrative of potential variations.

FIG. 7 illustrates another variation 70 which utilizes an arch 19 connecting one or more tooth retaining portions 21, 23, as described above. However, in this variation, the microphone unit 74 may be integrated within or upon the arch 19 separated from the transducer assembly 72. One or more wires 76 routed through arch 19 may electrically connect the microphone unit 74 to the assembly 72. Alternatively, rather than utilizing a wire 76, microphone unit 74 and assembly 72 may be wirelessly coupled to one another, as described above.

FIG. 8A shows another variation 80 which utilizes a connecting member 82 which may be positioned along the lingual or buccal surfaces of a patient's row of teeth to connect one or more tooth retaining portions 21, 23. Connecting member 82 may be fabricated from any number of non-toxic materials, such stainless steel, Nickel, Platinum, etc. and affixed or secured 84, 86 to each respective retaining portions 21, 23. Moreover, connecting member 82 may be shaped to be as non-obtrusive to the user as possible. Accordingly, connecting member 82 may be configured to have a relatively low-profile for placement directly against the lingual or buccal teeth surfaces. The cross-sectional area of connecting member 82 may be configured in any number of shapes so long as the resulting geometry is non-obtrusive to the user. FIG. 8B illustrates one variation of the cross-sectional area which may be configured as a square or rectangle 90. FIG. 8C illustrates another connecting member geometry configured as a semi-circle 92 where the flat portion may be placed against the teeth surfaces. FIGS. 8D and 8E illustrate other alternative shapes such as an elliptical shape 94 and circular shape 96. These variations are intended to be illustrative and not limiting as other shapes and geometries, as practicable, are intended to be included within this disclosure.

Figure 9:
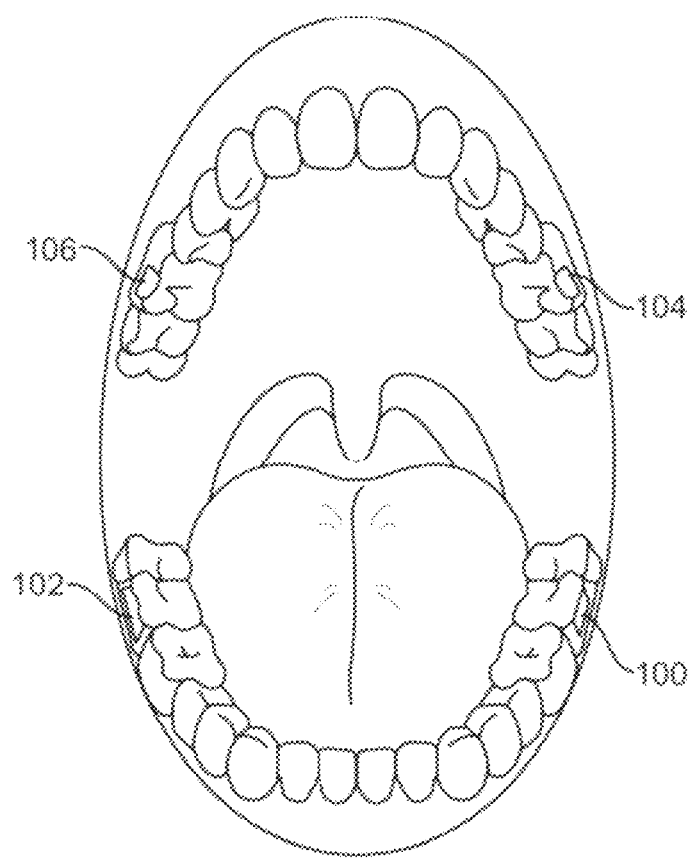
FIG. 9 shows yet another variation illustrating at least one microphone and optionally additional microphone units positioned around the user's mouth and in wireless communication with the electronics and/or transducer assembly.

In yet another variation for separating the microphone from the transducer assembly, FIG. 9 illustrates another variation where at least one microphone 102 (or optionally any number of additional microphones 104, 106) may be positioned within the mouth of the user while physically separated from the electronics and/or transducer assembly 100. In this manner, the one or optionally more microphones 102, 104, 106 may be wirelessly or by wire coupled to the electronics and/or transducer assembly 100 in a manner which attenuates or eliminates feedback from the transducer, also described in further detail below.

In utilizing multiple transducers and/or processing units, several features may be incorporated with the oral appliance(s) to effect any number of enhancements to the quality of the conducted vibratory signals and/or to emulate various perceptual features to the user to correlate auditory signals received by a user for transmitting these signals via sound conduction through teeth or bone structures in and/or around the mouth.

Figure 10:
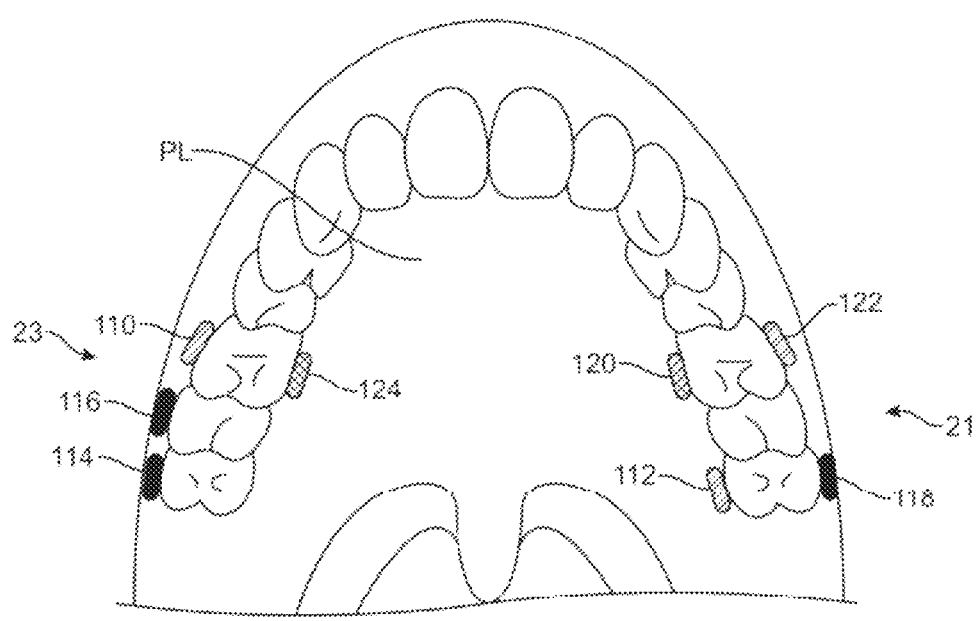
FIG. 10 illustrates yet another example of a configuration for positioning multiple transducers and/or processing units along a patient's dentition.

As illustrated in FIG. 10, another variation for positioning one or more transducers and/or processors is shown. In this instance generally, at least two microphones may be positioned respectively along tooth retaining portions 21, 23, e.g., outer microphone 110 positioned along a buccal surface of retaining portion 23 and inner microphone 112 positioned along a lingual surface of retaining portion 21. The one or more microphones 110, 112 may receive the auditory signals which are processed and ultimately transmitted through sound conductance via one or more transducers 114, 116, 118, one or more of which may be tuned to actuate only along certain discrete frequencies, as described in further detail below.

Moreover, the one or more transducers 114, 116, 118 may be positioned along respective retaining portions 21, 23 and configured to emulate directionality of audio signals received by the user to provide a sense of direction with respect to conducted audio signals. Additionally, one or more processors 120, 124 may also be provided along one or both retaining portions 21, 23 to process received audio signals, e.g., to translate the audio signals into vibrations suitable for conduction to the user, as well as other providing for other functional features. Furthermore, an optional processor 122 may also be provided along one or both retaining portions 21, 23 for interfacing and/or receiving wireless signals from other external devices such as an input control, as described above, or other wireless devices.

Figure 11A:
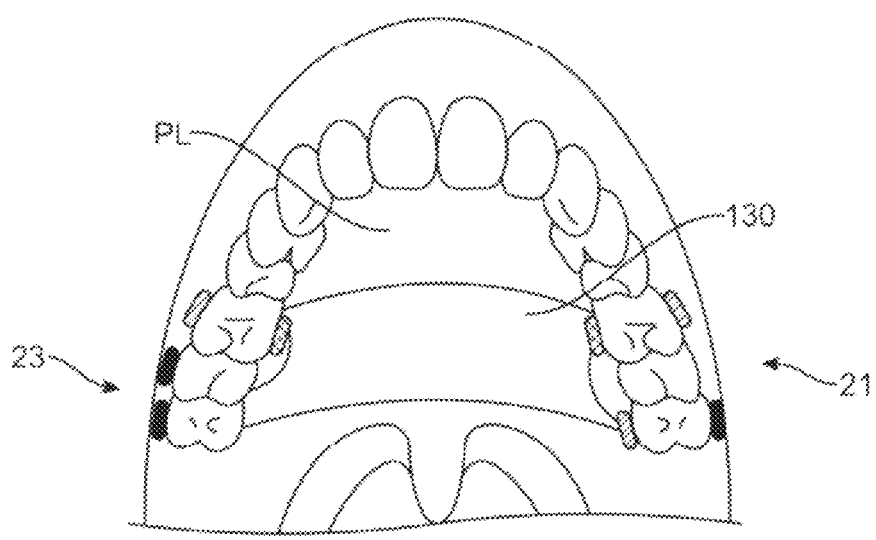
FIG. 11A illustrates another variation on the configuration for positioning multiple transducers and/or processors supported via an arched connector.
Figure 11B:
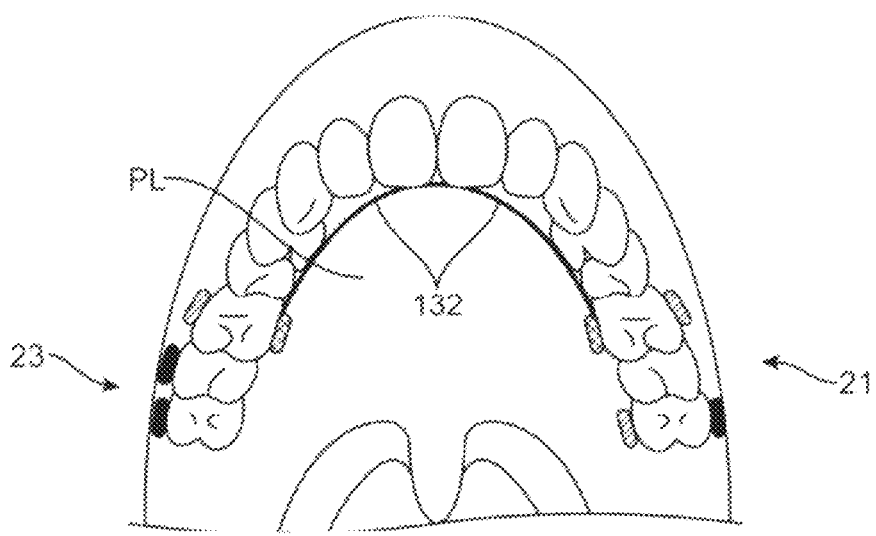
FIG. 11B illustrates another variation on the configuration utilizing a connecting member positioned along the lingual surfaces of a patient's dentition.

FIG. 11A illustrates another configuration utilizing an arch 130 similar to the configuration shown in FIG. 7 for connecting the multiple transducers and processors positioned along tooth retaining portions 21, 23. FIG. 11B illustrates yet another configuration utilizing a connecting member 132 positioned against the lingual surfaces of the user's teeth, similar to the configuration shown in FIG. 8A, also for connecting the multiple transducers and processors positioned along tooth retaining portions 21, 23.

In configurations particularly where the one or more microphones are positioned within the user's mouth, filtering features such as Acoustic Echo Cancellation (AEC) may be optionally utilized to eliminate or mitigate undesired sounds received by the microphones. AEC algorithms are well utilized and are typically used to anticipate the signal which may re-enter the transmission path from the microphone and cancel it out by digitally sampling an initial received signal to form a reference signal. Generally, the received signal is produced by the transducer and any reverberant signal which may be picked up again by the microphone is again digitally sampled to form an echo signal. The reference and echo signals may be compared such that the two signals are summed ideally at 180° out of phase to result in a null signal, thereby cancelling the echo.

Figure 12A:
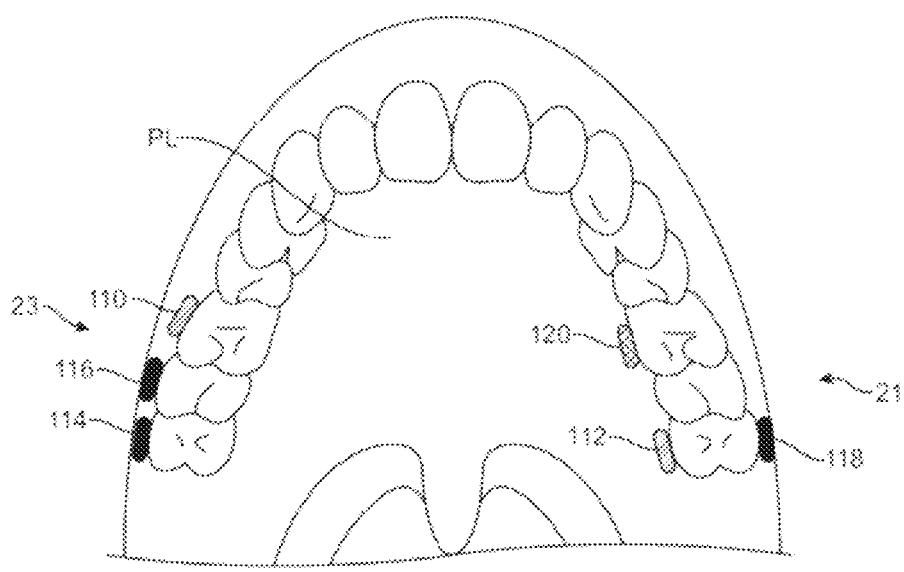
FIG. 12A shows a configuration for positioning one or more transducers with multiple microphones.

In the variation shown in FIG. 12A, at least two intrabuccal microphones 110, 112 may be utilized to separate out desired sounds (e.g., sounds received from outside the body such as speech, music, etc.) from undesirable sounds (e.g., sounds resulting from chewing, swallowing, breathing, self-speech, teeth grinding, etc.). If these undesirable sounds are not filtered or cancelled, they may be amplified along with the desired audio signals making for potentially unintelligible audio quality for the user. Additionally, desired audio sounds may be generally received at relatively lower sound pressure levels because such signals are more likely to be generated at a distance from the user and may have to pass through the cheek of the user while the undesired sounds are more likely to be generated locally within the oral cavity of the user.

Samples of the undesired sounds may be compared against desired sounds to eliminate or mitigate the undesired sounds prior to actuating the one or more transducers to vibrate only the resulting desired sounds to the user. In this example, first microphone 110 may be positioned along a buccal surface of the retaining portion 23 to receive desired sounds while second microphone 112 may be positioned along a lingual surface of retaining portion 21 to receive the undesirable sound signals. Processor 120 may be positioned along either retaining portion 21 or 23, in this case along a lingual surface of retaining portion 21, and may be in wired or wireless communication with the microphones 110, 112.

Figure 12B:
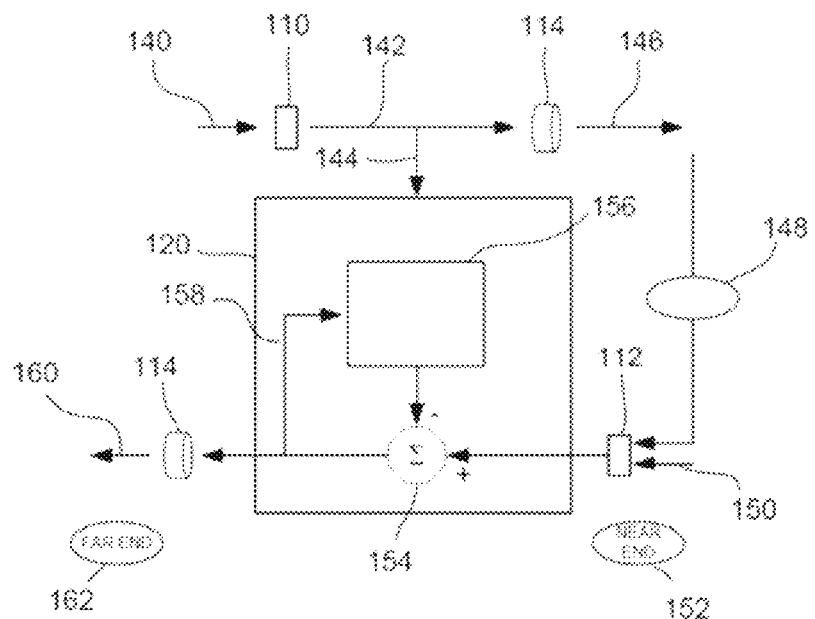
FIG. 12B schematically illustrates an example for integrating an acoustic echo cancellation system with the oral appliance.

Although audio signals may be attenuated by passing through the cheek of the user, especially when the mouth is closed, first microphone 110 may still receive the desired audio signals for processing by processor 120, which may also amplify the received audio signals. As illustrated schematically in FIG. 12B, audio signals for desired sounds, represented by far end speech 140, are shown as being received by first microphone 110. Audio signals for the undesired sounds 152, represented by near end speech 150, are shown as being received by second microphone 112. Although it may be desirable to position the microphones 110, 112 in their respective positions to optimize detection of their respective desirable and undesirable sounds, they may of course be positioned at other locations within the oral cavity as so desired or practicable. Moreover, while it may also be desirable for first and second microphone 110, 112 to detect only their respective audio signals, this is not required. However, having the microphones 110, 112 detect different versions of the combination of desired and undesired sounds 140, 150, respectively, may be desirable so as to effectively process these signals via AEC processor 120.

The desired audio signals may be transmitted via wired or wireless communication along a receive path 142 where the signal 144 may be sampled and received by AEC processor 120. A portion of the far end speech 140 may be transmitted to one or more transducers 114 where it may initially conduct the desired audio signals via vibration 146 through the user's bones. Any resulting echo or reverberations 148 from the transmitted vibration 146 may be detected by second microphone 112 along with any other undesirable noises or audio signals 150, as mentioned above. The undesired signals 148, 150 detected by second microphone 112 or the sampled signal 144 received by AEC processor 120 may be processed and shifted out of phase, e.g., ideally 180° out of phase, such that the summation 154 of the two signals results in a cancellation of any echo 148 and/or other undesired sounds 150.

The resulting summed audio signal may be redirected through an adaptive filter 156 and re-summed 154 to further clarify the audio signal until the desired audio signals is passed along to the one or more transducers 114 where the filtered signal 162, free or relatively free from the undesired sounds, may be conducted 160 to the user. Although two microphones 110, 112 are described in this example, an array of additional microphones may be utilized throughout the oral cavity of the user. Alternatively, as mentioned above, one or more microphones may also be positioned or worn by the user outside the mouth, such as in a bracelet, necklace, etc. and used alone or in combination with the one or more intrabuccal microphones. Furthermore, although three transducers 114, 116, 118 are illustrated, other variations may utilize a single transducer or more than three transducers positioned throughout the user's oral cavity, if so desired.

Independent from or in combination with acoustic echo cancellation, another processing feature for the oral appliance may include use of a multiband actuation system to facilitate the efficiency with which audio signals may be conducted to the user. Rather than utilizing a single transducer to cover the entire range of the frequency spectrum (e.g., 200 Hz to 10,000 Hz), one variation may utilize two or more transducers where each transducer is utilized to deliver sounds within certain frequencies. For instance, a first transducer may be utilized to deliver sounds in the 200 Hz to 2000 Hz frequency range and a second transducer may be used to deliver sounds in the 2000 Hz to 10,000 Hz frequency range. Alternatively, these frequency ranges may be discrete or overlapping. As individual transducers may be configured to handle only a subset of the frequency spectrum, the transducers may be more efficient in their design.

Additionally, for certain applications where high fidelity signals are not necessary to be transmitted to the user, individual higher frequency transducers may be shut off to conserve power. In yet another alternative, certain transducers may be omitted, particularly transducers configured for lower frequency vibrations.

Figure 13A:
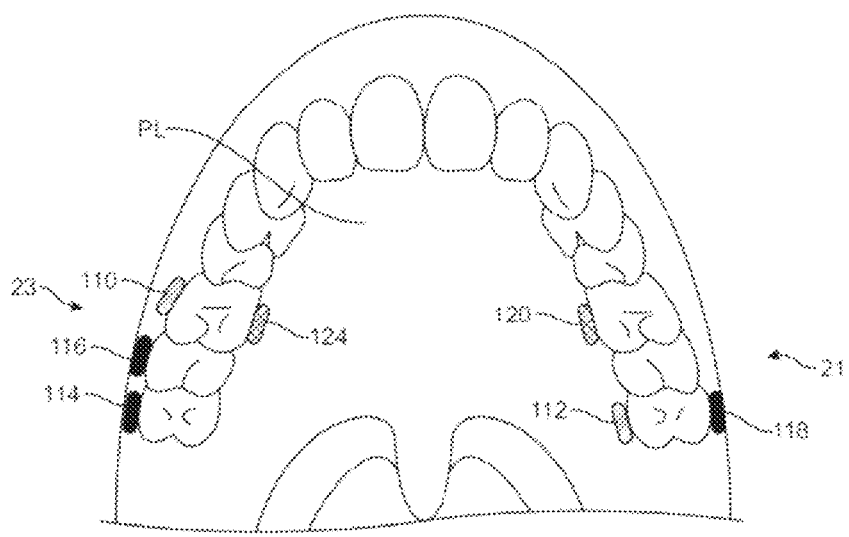
FIG. 13A shows a configuration for positioning and utilizing multiple band transducers with the oral appliance.

As illustrated in FIG. 13A, a configuration for utilizing multiple transducers is shown where individual transducers may be attuned to transmit only within certain frequency ranges. For instance, transducer 116 may be configured to transmit audio signals within the frequency range from, e.g., 200 Hz to 2000 Hz, while transducers 114 and/or 118 may be configured to transmit audio signals within the frequency range from, e.g., 2000 Hz to 10,000 Hz. Although the three transducers are shown, this is intended to be illustrative and fewer than three or more than three transducers may be utilized in other variations. Moreover, the audible frequency ranges are described for illustrative purposes and the frequency range may be sub-divided in any number of sub-ranges correlating to any number of transducers, as practicable. The choice of the number of sub-ranges and the lower and upper limits of each sub-range may also be varied depending upon a number of factors, e.g., the desired fidelity levels, power consumption of the transducers, etc.

One or both processors 120 and/or 124, which are in communication with the one or more transducers (in this example transducers 114, 116, 118), may be programmed to treat the audio signals for each particular frequency range similarly or differently. For instance, processors 120 and/or 124 may apply a higher gain level to the signals from one band with respect to another band. Additionally, one or more of the transducers 114, 116, 118 may be configured differently to optimally transmit vibrations within their respective frequency ranges. In one variation, one or more of the transducers 114, 116, 118 may be varied in size or in shape to effectuate an optimal configuration for transmission within their respective frequencies.

As mentioned above, the one or more of transducers 114, 116, 118 may also be powered on or off by the processor to save on power consumption in certain listening applications. As an example, higher frequency transducers 114, 118 may be shut off when higher frequency signals are not utilized such as when the user is driving. In other examples, the user may activate all transducers 114, 116, 118 such as when the user is listening to music. In yet another variation, higher frequency transducers 114, 118 may also be configured to deliver high volume audio signals, such as for alarms, compared to lower frequency transducers 116. Thus, the perception of a louder sound may be achieved just by actuation of the higher frequency transducers 114, 118 without having to actuate any lower frequency transducers 116.

Figure 13B:
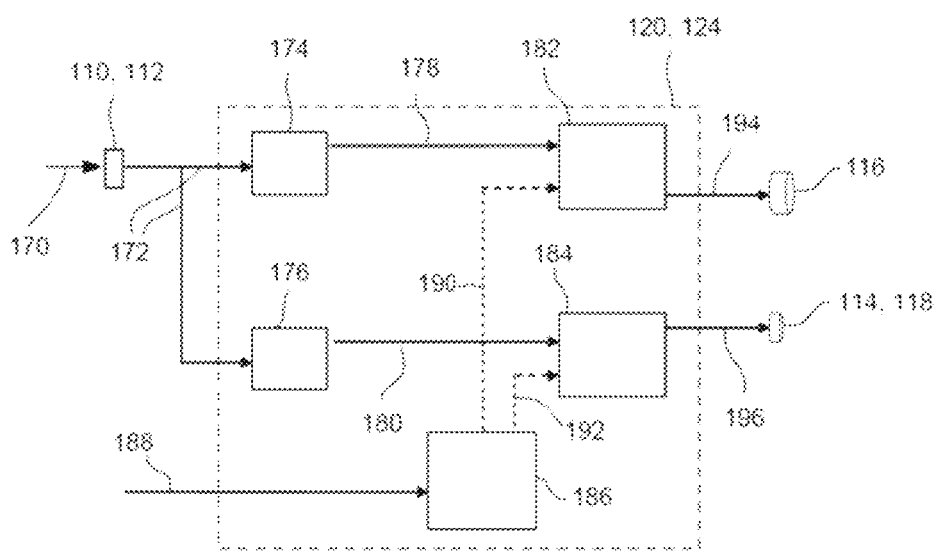
FIG. 13B schematically illustrates another example for integrating multiple band transducers with the oral appliance.

An example of how audio signals received by a user may be split into sub-frequency ranges for actuation by corresponding lower or higher frequency transducers is schematically illustrated in FIG. 13B. In this example, an audio signal 170 received by the user via microphones 110 and/or 112 may be transmitted 172 to one or more processors 120 and/or 124. Once the audio signals have been received by the respective processor, the signal may be filtered by two or more respective filters to transmit frequencies within specified bands. For instance, first filter 174 may receive the audio signal 172 and filter out the frequency spectrum such that only the frequency range between, e.g., 200 Hz to 2000 Hz, is transmitted 178. Second filter 176 may also receive the audio signal 172 and filter out the frequency spectrum such that only the frequency range between, e.g., 2000 Hz to 10,000 Hz, is transmitted 180.

Each respective filtered signal 178, 180 may be passed on to a respective processor 182, 184 to further process each band's signal according to an algorithm to achieve any desired output per transducer. Thus, processor 182 may process the signal 178 to create the output signal 194 to vibrate the lower frequency transducer 116 accordingly while the processor 184 may process the signal 180 to create the output signal 196 to vibrate the higher frequency transducers 114 and/or 118 accordingly. An optional controller 186 may receive control data 188 from user input controls, as described above, for optionally sending signals 190, 192 to respective processors 182, 184 to shut on/off each respective processor and/or to append ancillary data and/or control information to the subsequent transducers.

Figure 14A:
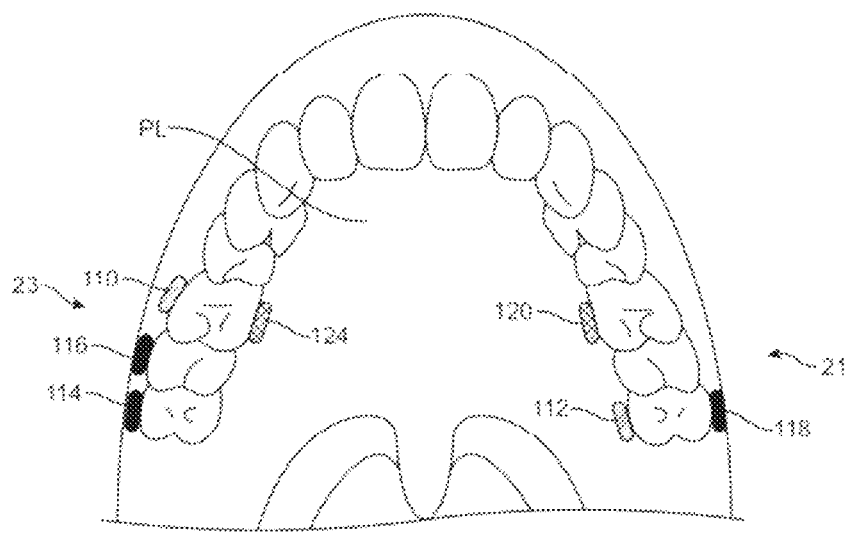
FIG. 14A shows a configuration for positioning multiple transducers for emulating directionality of audio signals perceived by a user.

In addition to or independent from either acoustic echo cancellation and/or multiband actuation of transducers, yet another process which may utilize the multiple transducers may include the utilization of directionality via the conducted vibrations to emulate the directional perception of audio signals received by the user. Generally, human hearing is able to distinguish the direction of a sound wave by perceiving differences in sound pressure levels between the two cochlea. In one example for providing the perception of directionality with an oral appliance, two or more transducers, such as transducers 114, 118, may be positioned apart from one another along respective retaining portions 21, 23, as shown in FIG. 14A.

One transducer may be actuated corresponding to an audio signal while the other transducer is actuated corresponding to the same audio signal but with a phase and/or amplitude and/or delay difference intentionally induced corresponding to a direction emulated for the user. Generally, upon receiving a directional audio signal and depending upon the direction to be emulated and the separation between the respective transducers, a particular phase and/or gain and/or delay change to the audio signal may be applied to the respective transducer while leaving the other transducer to receive the audio signal unchanged.

Figure 14B:
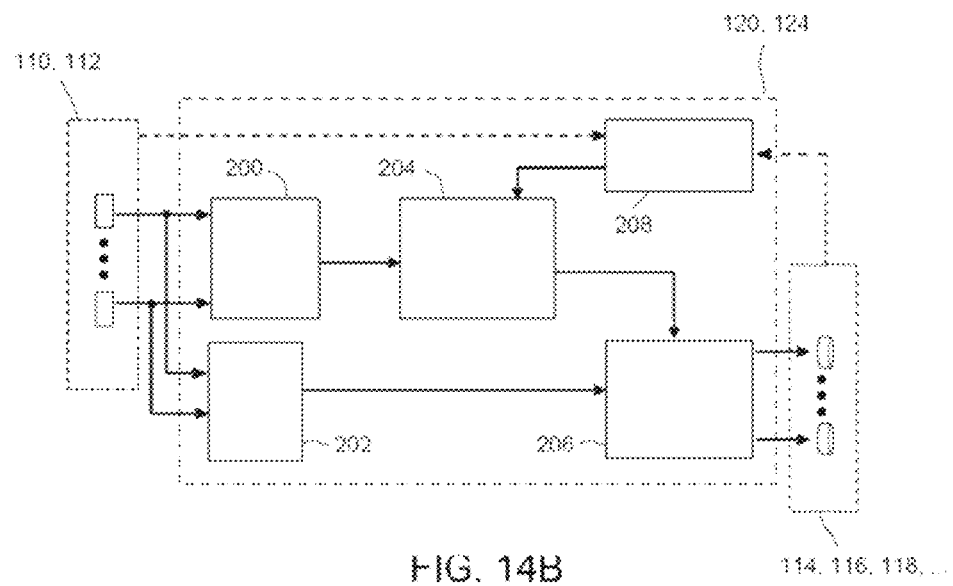
FIG. 14B schematically illustrates an example for emulating the directionality of detected audio signals via multiple transducers.

As illustrated in the schematic illustration of FIG. 14B, audio signals received by the one or more microphones 110, 112, which may include an array of intra-buccal and/or extra-buccal microphones as described above, may be transmitted wirelessly or via wire to the one or more processors 120, 124, as above. The detected audio signals may be processed to estimate the direction of arrival of the detected sound 200 by applying any number of algorithms as known in the art. The processor may also simply reproduce a signal that carries the information of the received sound 202 detected from the microphones 110, 112. This may entail a transfer of the information from one of the microphones, a sum of the signals received from the microphones, or a weighted sum of the signals received from the microphones, etc., as known in the art. Alternatively, the reproduced sound 202 may simply pass the information in the audio signals from any combination of the microphones or from any single one of the microphones, e.g., a first microphone, a last microphone, a random microphone, a microphone with the strongest detected audio signals, etc.

With the estimated direction of arrival of the detected sound 200 determined, the data may be modified for phase and/or amplitude and/or delay adjustments 204 as well as for orientation compensation 208, if necessary, based on additional information received the microphones 110, 112 and relative orientation of the transducers 114, 116, 118, as described in further detail below. The process of adjusting for phase and/or amplitude and/or delay 204 may involve calculating one phase adjustment for one of the transducers. This may simply involve an algorithm where given a desired direction to be emulated, a table of values may correlate a set of given phase and/or amplitude and/or delay values for adjusting one or more of the transducers. Because the adjustment values may depend on several different factors, e.g., speed of sound conductance through a user's skull, distance between transducers, etc., each particular user may have a specific table of values. Alternatively, standard set values may be determined for groups of users having similar anatomical features, such as jaw size among other variations, and requirements. In other variations, rather than utilizing a table of values in adjusting for phase and/or amplitude and/or delay 204, set formulas or algorithms may be programmed in processor 120 and/or 124 to determine phase and/or amplitude and/or delay adjustment values. Use of an algorithm could simply utilize continuous calculations in determining any adjustment which may be needed or desired whereas the use of a table of values may simply utilize storage in memory.

Figure 15:
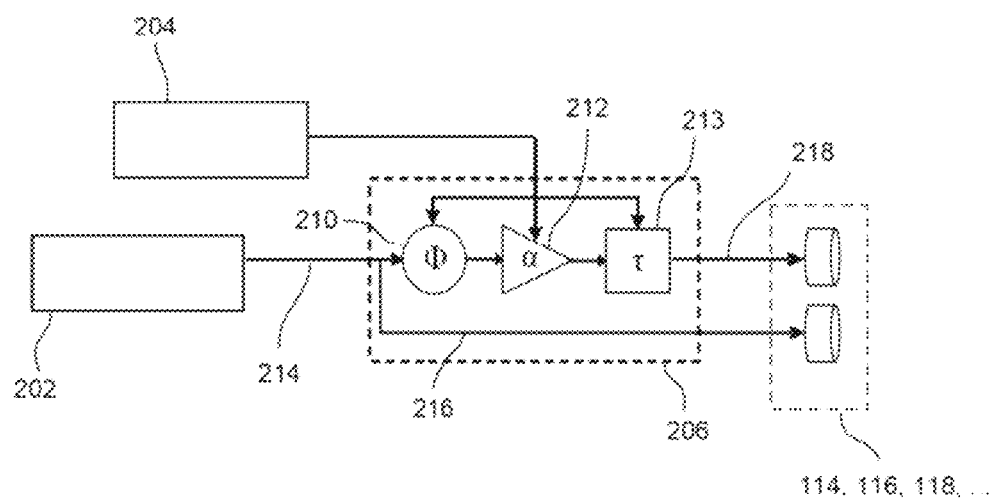
FIG. 15 schematically illustrates an example for activating one or more transducers to emulate directionality utilizing phase and/or amplitude modified signals.

Once any adjustments in phase and/or amplitude and/or delay 204 are determined and with the reproduced signals 202 processed from the microphones 110, 112, these signals may then be processed to calculate any final phase and/or amplitude and/or delay adjustments 206 and these final signals may be applied to the transducers 114, 116, 118, as illustrated, to emulate the directionality of received audio signals to the user. A detailed schematic illustration of the final phase and/or amplitude and/or delay adjustments 206 is illustrated in FIG. 15 where the signals received from 202 may be split into two or more identical signals 214, 216 which may correlate to the number of transducers utilized to emulate the directionality. The phase and/or amplitude and/or delay adjustments 204 may be applied to one or more of the received signals 214, 216 by applying either a phase adjustment (Φ) 210, e.g., any phase adjustment from 0° to 360°, and/or amplitude adjustment (α) 212, e.g., any amplitude adjustment from 1.0 to 0.7, and/or delay (τ) 213, e.g., any time delay of 0 to 125 μ-sec, to result in at least one signal 218 which has been adjusted for transmission via the one or more transducers. These values are presented for illustrative purposes and are not intended to be limiting. Although the adjustments may be applied to both signals 214, 216, they may also be applied to a single signal 214 while one of the received signals 216 may be unmodified and passed directly to one of the transducers.

Figure 16:
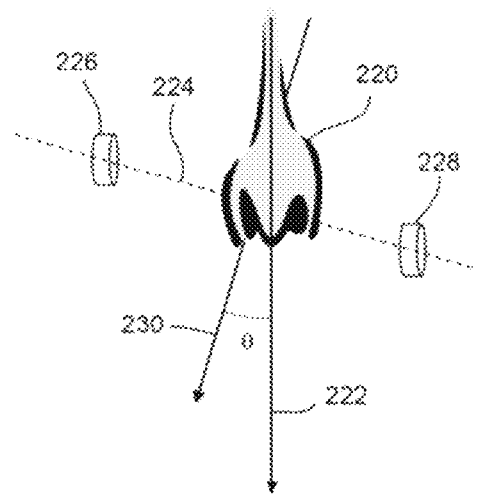
FIG. 16 schematically illustrates an example for optionally compensating for the relative positioning of the microphones with respect to the user for emulating directionality of perceived audio signals.

As mentioned above, compensating 208 for an orientation of the transducers relative to one another as well as relative to an orientation of the user may be taken into account in calculating any adjustments to phase and/or amplitude and/or delay of the signals applied to the transducers. For example, the direction 230 perpendicular to a line 224 connecting the microphones 226, 228 (intra-buccal and/or extra-buccal) may define a zero degree direction of the microphones. A zero degree direction' of the user's head may be indicated by the direction 222, which may be illustrated as in FIG. 16 as the direction the user's nose points towards. The difference between the zero degree direction of the microphones and the zero degree direction of the user's head may define an angle; Θ, which may be taken into account as a correction factor when determining the phase and/or amplitude adjustments. Accordingly, if the positioning of microphones 226, 228 are such that their zero degree direction is aligned with the zero degree direction of the user's head, then little or no correction may be necessary. If the positioning of the microphones 226, 228 is altered relative to the user's body and an angle is formed relative to the zero degree direction of the user's head, then the audio signals received by the user and the resulting vibrations conducted by the transducers to the user may be adjusted for phase and/or amplitude taking into account the angle, Θ, when emulating directionality with the vibrating transducers.

In addition to or independent from any of the processes described above, another feature which may utilize the oral appliance and processing capabilities may include the ability to vibrationally conduct ancillary audio signals to the user, e.g., the oral appliance may be configured to wirelessly receive and conduct signals from secondary audio sources to the user. Examples may include the transmission of an alarm signal which only the user may hear or music conducted to the user in public locations, etc. The user may thus enjoy privacy in receiving these ancillary signals while also being able to listen and/or converse in an environment where a primary audio signal is desired.

Figure 17A:
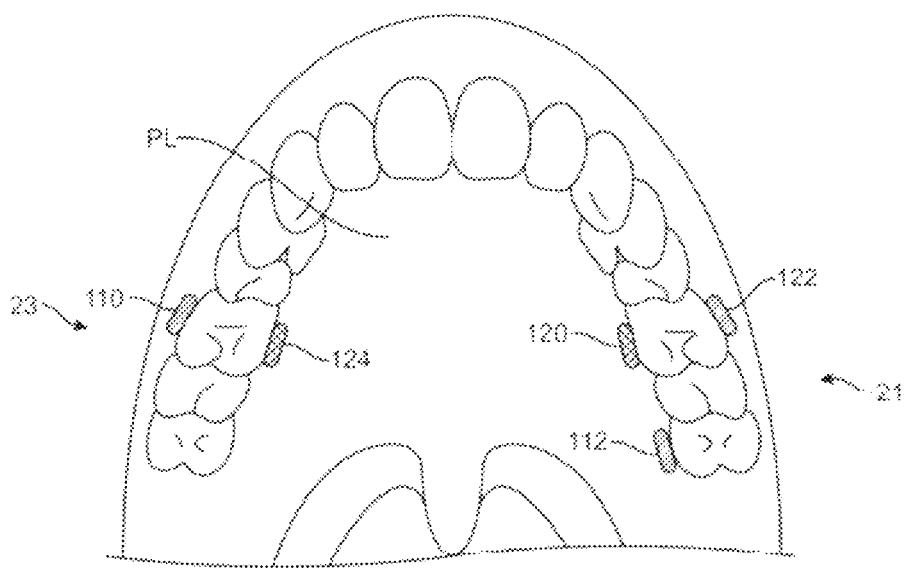
FIG. 17A shows a configuration for positioning multiple transducers which may be configured to provide for one or more ancillary auditory/conductance channels.
Figure 17B:
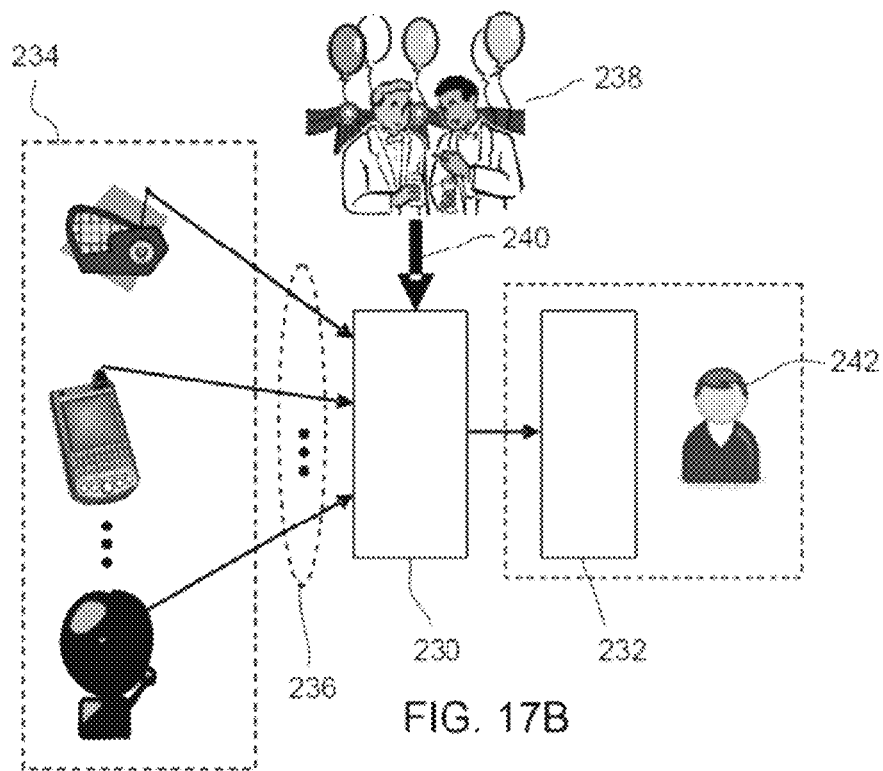
FIG. 17B schematically illustrates an example for providing one or more ancillary channels for secondary audio signals to be provided to a user.
Figure 17C:
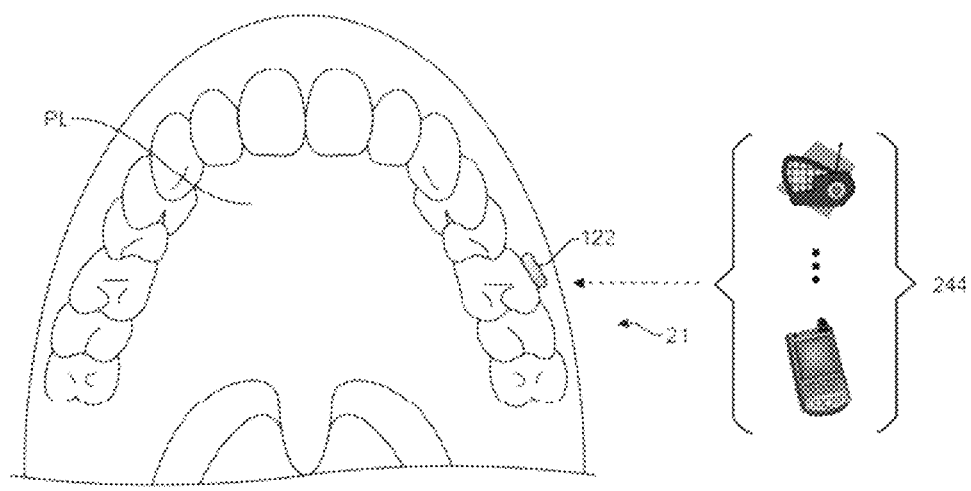
FIG. 17C illustrates another variation where secondary device may directly transmit audio signals wirelessly via the oral appliance.

FIG. 17A shows an example of placing one or more microphones 110, 112 as well as an optional wireless receiver 122 along one or both retaining portions 21, 23, as above. In a schematic illustration shown in FIG. 17B, one variation for receiving and processing multiple audio signals is shown where various audio sources 234, 238 (e.g., alarms, music players, cell phones, PDA's, etc.) may transmit their respective audio signals 236, 240 to an audio receiver processor 230, which may receive the sounds via the one or more microphones and process them for receipt by an audio application processor 232, which may apply the combined signal received from audio receiver processor 230 and apply them to one or more transducers to the user 242. FIG. 17C illustrates another variation where a wireless receiver and/or processor 122 located along one or more of the retaining portions 21 may be configured to wirelessly receive audio signals from multiple electronic audio sources 244. This feature may be utilized with any of the variations described herein alone or in combination.

Figure 18:
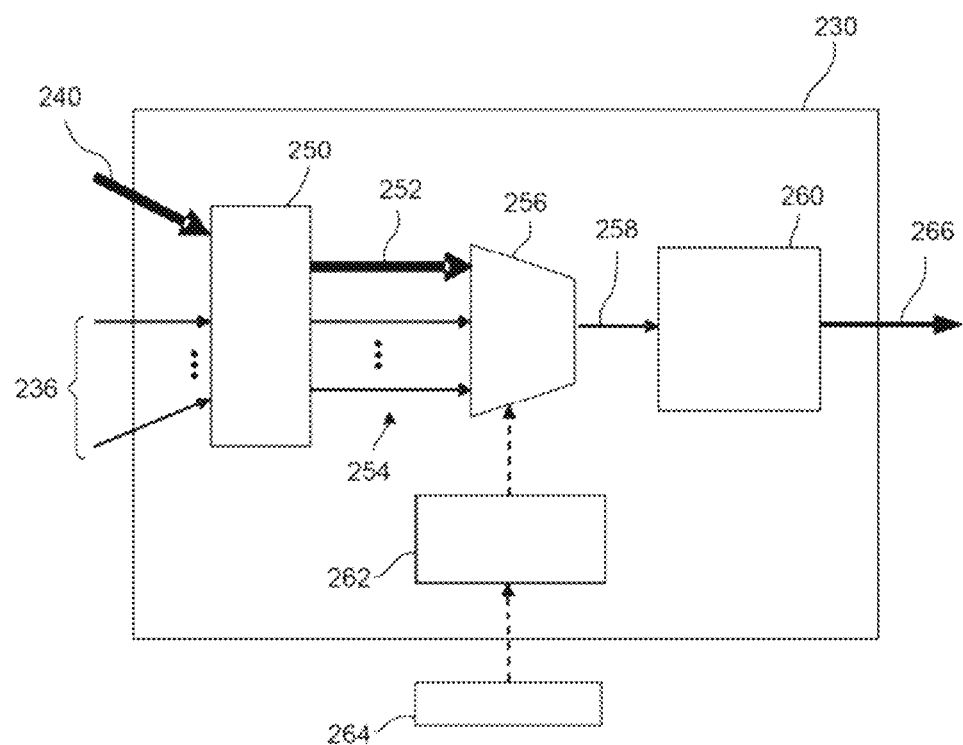
FIG. 18 schematically illustrates an example for optionally adjusting features of the device such as the manner in which ancillary auditory signals are transmitted to the user.

The audio receiver processor 230 may communicate wirelessly or via wire with the audio application processor 232. During one example of use, a primary audio signal 240 (e.g., conversational speech) along with one or more ancillary audio signals 236 (e.g., alarms, music players, cell phones, PDA's, etc.) may be received by the one or more microphones of a receiver unit 250 of audio receiver processor 230. The primary signal 250 and ancillary signals 254 may be transmitted electrically to a multiplexer 256 which may combine the various signals 252, 254 in view of optional methods, controls and/or priority data 262 received from a user control 264, as described above. Parameters such as prioritization of the signals as well as volume, timers, etc., may be set by the user control 264. The multiplexed signal 258 having the combined audio signals may then be transmitted to processor 260, which may transmit the multiplexed signal 266 to the audio application processor 232, as illustrated in FIG. 18.

Figure 19A:
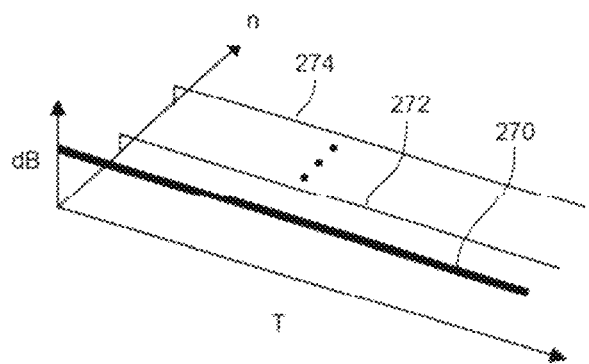
FIG. 19A illustrates one method for delivering ancillary audio signals as vibrations transmitted in parallel.

As described above, the various audio signals 236, 240 may be combined and multiplexed in various forms 258 for transmission to the user 242. For example, one variation for multiplexing the audio signals via multiplexer 256 may entail combining the audio signals such that the primary 240 and ancillary 236 signals are transmitted by the transducers in parallel where all audio signals are conducted concurrently to the user, as illustrated in FIG. 19A, which graphically illustrates transmission of a primary signal 270 in parallel with the one or more ancillary signals 272, 272 over time, T. The transmitted primary signal 270 may be transmitted at a higher volume, i.e., a higher dB level, than the other ancillary signals 272, 274, although this may be varied depending upon the user preferences.

Figure 19B:
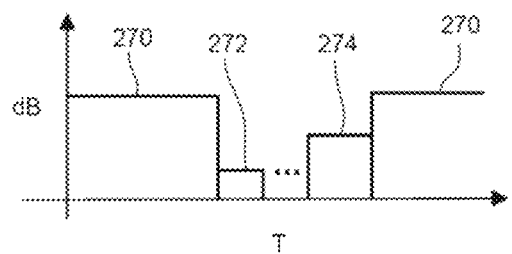
FIG. 19B illustrates another method for delivering ancillary audio signals as vibrations transmitted in series.

Alternatively, the multiplexed signal 258 may be transmitted such that the primary 240 and ancillary 236 signals are transmitted in series, as graphically illustrated in FIG. 19B. In this variation, the transmitted primary 270 and ancillary 272, 274 signals may be conducted to the user in a pre-assigned, random, preemptive, or non-preemptive manner where each signal is conducted serially.

Figure 19C:
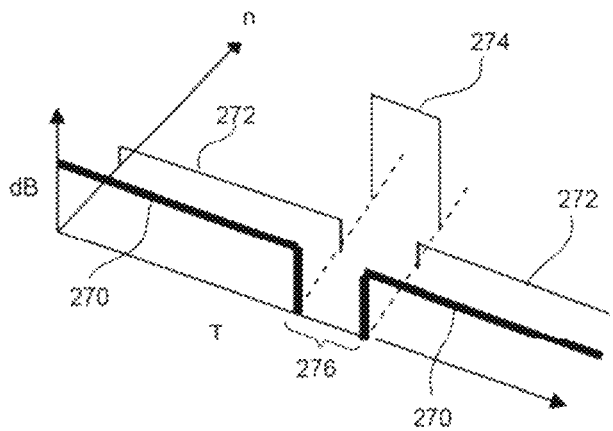
FIG. 19C illustrates yet another method for delivering ancillary audio signals as vibrations transmitted in a hybrid form utilizing signals transmitted in both parallel and series.

In yet another example, the transmitted signals may be conducted to the user in a hybrid form combining the parallel and serial methods described above and as graphically illustrated in FIG. 19C. Depending on user settings or preferences, certain audio signals 274, e.g., emergency alarms, may preempt primary 270 and/or ancillary 272 signals from other sources at preset times 276 or intermittently or in any other manner such that the preemptive signal 274 is played such that it is the only signal played back to the user.

The applications of the devices and methods discussed above are not limited to the treatment of hearing loss but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:
1. An apparatus for transmitting vibrations, comprising:
    a transducer housing that is configured to engage a first side of at least one tooth, wherein the first side is a lingual or a buccal side of the at least one tooth;

an actuatable transducer disposed within the transducer housing and configured to transmit vibrations to the at least one tooth;

an electronics housing that is configured to engage a second side of the at least one tooth, wherein the second side is opposite the first side of the at least one tooth; and an electronics assembly disposed within the electronics housing, wherein the transducer housing and the electronics housing produce an interference fit between the apparatus and the first side and second side of the at least one tooth and thereby secure the apparatus to the at least one tooth.

2. The apparatus of claim 1, wherein the transducer housing and/or the electronics housing comprise a polymer.

3. The apparatus of claim 1, wherein the apparatus is configured to omit an occlusal surface.

4. The apparatus of claim 1, wherein the actuatable transducer comprises a piezoelectric element.

5. The apparatus of claim 1, wherein the electronic assembly comprises a processor and/or a rechargeable power supply.

6. The apparatus of claim 1, wherein. the electronic assembly comprises a receiver in wireless communication with a transmitter.

7. The apparatus of claim 1, further comprising at least one microphone in communication with the electronics assembly for receiving an auditory signal.

8. The apparatus of claim 7, wherein the at least one microphone is positioned within or upon the apparatus.

9. The apparatus of claim 7, wherein the at least one microphone comprises an intra-buccal microphone.

10. The apparatus of claim 7, further comprising a second microphone for receiving a second auditory signal.

11. An apparatus for transmitting vibrations, comprising:

a transducer housing that is configured to engage a first side of at least one tooth, wherein the first side is a lingual or a buccal side of the at least one tooth;

an actuatable transducer disposed within the transducer housing and configured to transmit vibrations to the at least one tooth;

an electronics housing that is configured to engage a second side of the at least one tooth, wherein the second side is opposite the first side of the at least one tooth; and an electronics assembly disposed within the electronics housing; and at least one microphone in communication with the electronics assembly for receiving an auditory signal, wherein the transducer housing and the electronics housing produce an interference fit between the apparatus and the at least one tooth.

12. The apparatus of claim 11, wherein the at least one microphone is positioned within or upon the apparatus.

13. The apparatus of claim 11, wherein the at least one microphone comprises an intra-buccal microphone.

14. The apparatus of claim 11, further comprising a second microphone for receiving a second auditory signal.

15. The apparatus of claim 11, wherein the transducer housing, and/or the electronics housing comprise a polymer.

16. The apparatus of claim 11, wherein the apparatus is configured to omit an occlusal surface.

17. The apparatus of claim 11, wherein the actuatable transducer comprises a piezoelectric element.

18. The apparatus of claim 11, wherein the electronic assembly comprises a processor and/or a rechargeable power supply.

19. The apparatus of claim 11, wherein the electronic assembly comprises a receiver in wireless communication with a transmitter.

20. The apparatus of claim 11, further comprising at least one microphone in communication with the electronics assembly for receiving an auditory signal.

21. An apparatus for transmitting vibrations, comprising:

a transducer housing that is configured to engage a first side of at least one tooth, wherein the first side is a lingual or a buccal side of the at least one tooth;

an actuatable transducer disposed within the transducer housing and configured to transmit vibrations to the at least one tooth;

an electronics housing that is configured to engage a second side of the at least one tooth, wherein the second side is opposite the first side of the at least one tooth; and an electronics assembly disposed within the electronics housing; and at least one microphone in communication with the electronics assembly for receiving an auditory signal, wherein the transducer housing and the electronics housing produce an interference fit between the apparatus and the first side and second side of the at least one tooth and thereby secure the apparatus to the at least one tooth.

22. The apparatus of claim 21, wherein the at least one microphone is positioned within or upon the apparatus.

23. The apparatus of claim 21, wherein the at least one microphone comprises an intra-buccal microphone.

24. The apparatus of claim 21, further comprising a second microphone for receiving a second auditory signal.

25. The apparatus of claim 21, wherein the transducer housing and/or the electronics housing comprise a polymer.

26. The apparatus of claim 21, wherein the apparatus is configured to omit an occlusal surface.

27. The apparatus of claim 21, wherein the actuatable transducer comprises a piezoelectric element.

28. The apparatus of claim 21, wherein the electronic assembly comprises a processor and/or a rechargeable power supply.

29. The apparatus of claim 21, wherein the electronic assembly comprises a receiver in wireless communication with a transmitter.

30. The apparatus of claim 21, further comprising at least one microphone in communication with t he electronics assembly for receiving an auditory signal.

* * * * *